United States Patent
Zhang et al.

(10) Patent No.: US 8,148,385 B2
(45) Date of Patent: Apr. 3, 2012

(54) SUBSTITUTED [1,2,3] TRIAZOLO[4,5-D]PYRIMIDINE DERIVATIVES AS ADP $P2Y_{12}$ RECEPTOR ANTAGONISTS

(75) Inventors: Han-Cheng Zhang, Lansdale, PA (US); Bruce E. Maryanoff, Forest Grove, PA (US); Hong Ye, Lansdale, PA (US); Cailin Chen, New Hope, PA (US)

(73) Assignee: Janssen Pharmaceutica N.V. (BE)

( * ) Notice: Subject to any disclaimer, the term of this patent is extended or adjusted under 35 U.S.C. 154(b) by 866 days.

(21) Appl. No.: 11/980,907

(22) Filed: Oct. 31, 2007

(65) Prior Publication Data

US 2008/0312257 A1 Dec. 18, 2008

Related U.S. Application Data

(60) Provisional application No. 60/855,623, filed on Oct. 31, 2006.

(51) Int. Cl.
*C07D 487/04* (2006.01)
*A61K 31/519* (2006.01)
*A61P 7/02* (2006.01)
*A61P 9/10* (2006.01)
*A61P 37/06* (2006.01)
*A61P 25/06* (2006.01)

(52) U.S. Cl. ..................... 514/261.1; 544/254
(58) Field of Classification Search .................. 544/254; 514/261.1
See application file for complete search history.

(56) References Cited

U.S. PATENT DOCUMENTS

| | | | |
|---|---|---|---|
| 4,076,711 | A | 2/1978 | Ganguly et al. |
| 6,107,300 | A | 8/2000 | Bakthavatchalam et al. |
| 6,448,261 | B1 | 9/2002 | Bakthavatchalam et al. |
| 6,458,796 | B1 | 10/2002 | Haning et al. |

FOREIGN PATENT DOCUMENTS

| | | |
|---|---|---|
| WO | WO 97/35539 A2 | 10/1997 |
| WO | WO 98/28300 | 7/1998 |
| WO | WO 99/05142 A1 | 2/1999 |
| WO | WO 2004/018473 A2 | 3/2004 |
| WO | WO 2004/018473 A3 | 3/2004 |

OTHER PUBLICATIONS

Koppel et al, "Potential Purine Antagonists, XIX, Synthesis of Some 9-Alkyl(aryl)-2-amino-6-substituted Purines and Related v-Triazolo[d] pyrimidines," Journal of the American Chemical Society, 1959, pp. 3046-3051, vol. 81, Contribution from Dept. of Chemistry, Arizona State University.

Biagi et al, "erythro- and threo-2-Hydroxynonyl substituted 2-phenyladenines and 2-phenyl-8-azaadenines: ligands for $A_1$ adenosine receptors and adenosine deaminase," IL FARMACO, 2002, pp. 221-233, vol. 57, Elsevier.

Leese et al, "Potential Anti-purines. Part II. The synthesis of 6- and 9-Substituted Purines and 8-Azapurines," Journal of the Chemical Society, Abstracts, 1958, pp. 4107-4110, 804.

Konkel et al, "and Biological activity of Cyclohexenyl . . . ," Nucleosides, 1995, pp. 2061-2077, 14 (9&10).

Kotva et al, "Substances with Antineoplastic Activity. XLL 5-(8-Aza-6-Purinylthio) Valeric Acid and Some of Its 9-Alkyl and 9-Cycloalkyl Derivatives," Collection of Czechoslovak Chem. Communications, 1970, pp. 1610-1613, vol. 35 (5).

Konkel et al, Palladium-Catalyzed Allylic Coupling of 1,2,3-Triazolo [4,5-*d*] pyrimidines (8-Azapurines), J. Org. Chem., 1996, pp. 6199-6204, vol. 61, American Chemical Society.

Kotva et al, "N(6) or N(9) Substituted 2-Phenyl-8-Azaadenines: Affinity for $A_1$ Adenosine Receptors. VII," IL FARMACO, 1995, pp. 659-667, 50 (10).

Biagi et al, "N(9)-Substituted 2-Phenyl-N(6)-Benzyl-8-Azaadenines: A1 Adenosine Receptor Affinity. A Comparison With the Corresponding N(6)-Substituted 2-Phenyl_N(9)-Benzyl-8-Azaadenines," IL FARMACO, 1996, pp. 395-399, 51 (6).

Design of Prodrugs, Ed. H. Bundgaard, Elsevier, 1985.

Teran et al, "Purine Derivatives of 1,2-Disubstituted Cyclohexane Analogues of Nucleosides," Nucleosides, Nucleotides & Nucleic Acids, 2003, pp. 787-789, vol. 22, Nos. 5-8.

Ramesh, et al., "Synthesis of Hydroxylated Cyclohexenyl-and Cyclohexanyladenines as Potential Inhibitors of S-Adenosylhomocysteine Hydrolase", J. Org. Chem., 1992, pp. 5861-5868, vol. 57.

International Search Report, PCTUS2007/023016, dated Apr. 11, 2008.

*Primary Examiner* — Susanna Moore
(74) *Attorney, Agent, or Firm* — Yuriy P. Stercho

(57) ABSTRACT

The present invention is directed to novel bicyclic triazolopyrimidine compounds of Formula (I) or a form thereof:

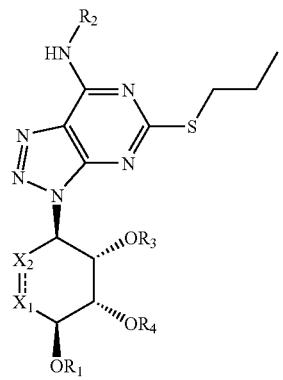

wherein $X_1$, $X_2$, $R_1$, $R_2$, $R_3$ and $R_4$ are as defined herein, and their methods of preparation and use as ADP inhibitors.

11 Claims, No Drawings

SUBSTITUTED [1,2,3] TRIAZOLO[4,5-D]PYRIMIDINE DERIVATIVES AS ADP P2Y$_{12}$ RECEPTOR ANTAGONISTS

CROSS REFERENCE TO RELATED APPLICATIONS

This present application claims benefit of U.S. Provisional Patent Application Ser. No. 60/855,623, filed Oct. 31, 2006, which is incorporated herein by reference in its entirety and for all purposes.

FIELD OF THE INVENTION

The present invention is directed to novel triazolopyrimidine compounds or forms thereof, their methods of preparation and use as ADP P2Y$_{12}$ receptor antagonists and platelet aggregation inhibitors for treating a platelet-mediated thrombotic disorder.

BACKGROUND OF THE INVENTION

Agonist-induced platelet activation results in platelet-endothelium and platelet-platelet interactions that lead to platelet aggregation, a process responsible for thrombus or hemostatic plug formation. Although the process plays an important role in repairing damaged vessel walls or wound healing, aberrant platelet aggregation is pathophysiological for arterial thrombosis.

Thrombosis is one of the main causes of death in the world and is involved in various disease conditions, such as cardiac infarction, unstable angina pectoris, stable angina pectoris, transitory ischemic attacks (TIA), stroke, peripheral arterial occlusion diseases, re-occlusions and restenosis after angioplasty or aortocoronary bypass, deep vein thromboses and arteriosclerosis.

A number of converging pathways lead to platelet aggregation, the final common event in which is a cross linking of platelets resulting from the binding of fibrinogen to the glycoprotein IIb/IIIa (GPIIb/IIIa) membrane binding site. The high anti-platelet aggregation efficacy of antibodies or antagonists for GPIIb/IIIa interferes with the binding of fibrinogen and also results in the adverse bleeding events observed with this class of agent. Thrombin can produce platelet aggregation largely independently of other pathways but substantial quantities of thrombin are unlikely to be present without prior activation of platelets by other mechanisms.

ADP (adenosine 5'-diphosphate) acts as a key mediator for thrombosis. A pivotal role for ADP is supported by the fact that other agents, such as adrenaline and 5-hydroxytryptamine (5HT, serotonin) will only produce aggregation in the presence of ADP. The limited anti-thrombotic activity of aspirin may reflect the fact that it blocks only one source of ADP released in a thromboxane-dependent manner following platelet adhesion. Aspirin has no effect on aggregation produced by other sources of ADP, such as damaged cells or ADP released under conditions of turbulent blood flow. ADP-induced platelet aggregation is induced by the purinoceptor P$_{2T}$ subtype receptor located on the platelet membrane.

Further, ADP released from aggregated platelet dense granules induces secondary aggregation via the feedback process that amplifies and propagates platelet activation induced by other agonists, such as collagen, thromboxin, 5HT, and serotonin. The inhibition of platelet aggregation induced by ADP is one of several antiplatelet drug mechanisms used for reducing the risk of clinical arterial and venous thrombotic events.

Current evidence suggests that there are three types of ADP receptor on platelet surfaces, classified as P2X$_1$, P2Y$_1$, and P2Y$_{12}$ (also referred to as P$_{2T}$, P2T$_{AC}$, P2Y$_{ADP}$, or P2$_{cyc}$) receptors.

The P2Y$_1$ receptor is linked to activation of phospholipase C via the G$_q$ protein and elevated cytosolic calcium and calcium influx via formation of IP$_3$ and release of Ca$^{++}$ from intracellular stores. These are involved in shape changes and transient aggregation. The P2Y$_{12}$ receptor has been characterized pharmacologically using selective antagonists as the receptor linked via G$_i$ to inhibition of adenylate cyclase. Accordingly, the P2Y$_{12}$ receptor mediates a fall in the cyclic AMP level in response to ADP that further mediates degranulation and sustained aggregation.

Therefore, an ADP P2Y$_{12}$ receptor antagonist would provide a more efficacious anti-thrombotic agent than aspirin or currently available therapies but with less profound effects on bleeding than other antagonists of the fibrinogen receptor.

PCT Application WO97/35539 (see U.S. Pat. Nos. 6,107, 300 and 6,448,261) describes the preparation of arylamino fused pyridines and pyrimidines as CRF antagonists. U.S. Pat. No. 4,076,711 describes triazolopyrimidine compounds for the topical treatment of psoriasis. U.S. Pat. No. 6,458,796 describes triazolopyrimidine compounds as inhibitors of cGMP metabolizing phosphodiesterases. PCT Application WO04/018473 describes azapurine derivatives as cyclin-dependent kinase inhibitors.

The article v-Triazolo[4,5-d]pyrimidines (8-azapurines). Part 18. Three new reactions for synthesizing 8-azapurinethiones from 4-amino-5-cyano-1,2,3-triazoles (Adrien A., Lin C. J., *Journal of the Chemical Society*, Perkin Transactions 1: Organic and Bio-Organic Chemistry (1972-1999) (1977), (2), 210-13) describes a 3,4-dihydro-7-(phenylamino)-3-(phenylmethyl)-5H-1,2,3-triazolo[4,5-d]pyrimidine-5-thione compound.

Each of the following references describes cyclohexyl substituted triazolopyrimidine compounds: Teran C., Santana L., Uriarte E., Vina D., De Clercq E., Purine Derivatives of 1,2-Disubstituted Cyclohexane Analogues of Nucleosides, *Nucleosides, Nucleotides & Nucleic Acids*, (2003), 22(5-8), 787-789; Biagi G., Giorgi I., Livi O., Pacchini F., Rum P., Scartoni V., Costa B., Mazzoni M., Giusti, L., erythro- and threo-2-Hydroxynonyl substituted 2-phenyladenines and 2-phenyl-8-azaadenines: ligands for A1 adenosine receptors and adenosine deaminase, *Farmaco*, (2002), 57(3), 221-233; Biagi G., Giorgi I., Livi O., Scartoni V., Lucacchini A., N(9)-substituted 2-phenyl-N(6)-benzyl-8-azaadenines: A1 adenosine receptor affinity. A comparison with the corresponding N(6)-substituted 2-phenyl-N(9)-benzyl-8-azaadenines, *Farmaco*, (1996), 51(6), 395-399; Biagi G., Giorgi I., Livi O., Scartoni V., Breschi C., Martini C., Scatizzi, R., N(6) or N(9) substituted 2-phenyl-8-azaadenines: affinity for A1 adenosine receptors. VII, *Farmaco*, (1995), 50(10), 659-67; Kotva R., Semonsky M., Vachek J., Jelinek V., Substances with antineoplastic activity. XLI. δ-(8-Aza-6-purinylthio)valeric acid and some of its 9-alkyl and 9-cycloalkyl derivatives, *Collection of Czechoslovak Chemical Communications*, (1970), 35(5), 1610-13; Koppel H. C., O'Brien D. E., Robins, R. K., Potential purine antagonists. XIX. Synthesis of some 9-alkyl(aryl)-2-amino-6-substituted purines and related v-triazolo[d]pyrimidines, *Journal of the American Chemical Society*, (1959), 81, 3046-51; Leese C. L., Timmis G. M., Potential antipurines. II. Synthesis of 6- and 9-substituted purines and 8-azapurines, *Journal of the Chemical Society*, Abstracts, (1958) 4107-10

Each of the following references describes cyclohexenyl substituted triazolopyrimidine compounds: Konkel M. J., Vince R., Palladium-Catalyzed Allylic Coupling of 1,2,3-Triazolo[4,5-d]pyrimidines (8-Azapurines), *Journal of Organic Chemistry*, (1996), 61(18), 6199-6204; and, Konkel M. J., Vince R., Synthesis and biological activity of cyclohexenyl nucleosides. cis-5-(9H-Purin-9-yl)-3-cyclohexenyl carbinols and their 8-azapurinyl analogs, *Nucleosides & Nucleotides*, (1995), 14(9 & 10), 2061-77.

SUMMARY OF THE INVENTION

The present invention is directed to a compound of Formula (I) or a form thereof:

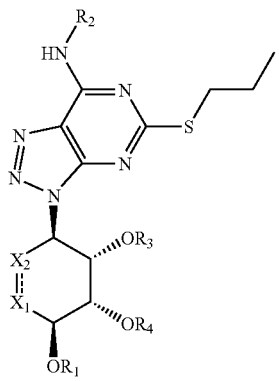

(I)

wherein $X_1$, $X_2$, $R_1$, $R_2$, $R_3$ and $R_4$ are as defined herein. Compounds of Formula (I) are useful as ADP $P2Y_{12}$ receptor antagonists.

The present invention is further directed to a method for ameliorating, treating or preventing a platelet-mediated thrombotic disease, disorder or condition in a subject in need thereof comprising administering to the subject an effective amount of a compound of Formula (I) or a form thereof.

This invention is also directed to a method for inhibiting platelet aggregation in a subject in need thereof comprising administering to the subject an effective amount of a compound of Formula (I) or a form thereof.

DETAILED DESCRIPTION OF THE INVENTION

The present invention provides a compound of Formula (I):

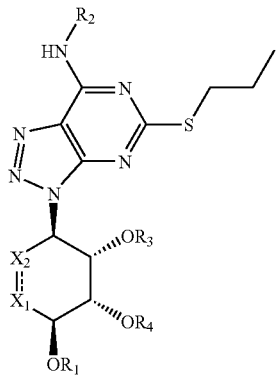

(I)

or a form thereof, wherein:

$R_1$ is selected from hydrogen, hydroxy-$C_{1-8}$alkyl, $C_{1-8}$alkoxy-$C_{1-8}$alkyl or carboxy-$C_{1-8}$alkyl;

$R_2$ is selected from $C_{1-8}$alkyl, $C_{1-8}$alkoxy-$C_{1-8}$alkyl, $C_{1-8}$alkyl-thio-$C_{1-8}$alkyl, $C_{3-8}$cycloalkyl, $C_{3-8}$cycloalkyl-$C_{1-8}$alkyl, phenyl-$C_{1-8}$alkyl, heterocyclyl, heterocyclyl-$C_{1-8}$alkyl, heteroaryl-$C_{1-8}$alkyl or halo-$C_{1-8}$alkyl, wherein each instance of $C_{3-8}$cycloalkyl, heterocyclyl and heteroaryl is optionally substituted with $C_{1-8}$alkyl, phenyl or benzyl, wherein phenyl is optionally substituted with $C_{1-4}$alkyl, $C_{1-4}$alkoxy, amino, $C_{1-4}$alkyl-amino, hydroxy, cyano, halo-$C_{1-4}$alkyl or halogen;

$R_3$ and $R_4$ are each selected from hydrogen or are optionally taken together with the carbon atoms of attachment to form a heterocyclyl ring having 5 or 6 ring members, wherein said heterocyclyl ring is optionally substituted with one or two $C_{1-8}$alkyl substituents; and, $X_1$ and $X_2$ are each selected from CH, $CH_2$ or CH(OH), wherein when either $X_1$ or $X_2$ is CH, then $X_1$ and $X_2$ must both be CH and the dashed line represents a double bond.

An example of the present invention is a compound of Formula (I) and a form thereof wherein $R_1$ is selected from hydrogen, hydroxy-$C_{1-8}$alkyl or carboxy-$C_{1-8}$alkyl.

An example of the present invention is a compound of Formula (I) and a form thereof wherein $R_1$ is selected from hydrogen, hydroxy-$C_{1-4}$alkyl or carboxy-$C_{1-4}$alkyl.

An example of the present invention is a compound of Formula (I) and a form thereof wherein $R_1$ is selected from hydrogen or hydroxy-$C_{1-4}$alkyl.

An example of the present invention is a compound of Formula (I) and a form thereof wherein $R_1$ is hydrogen or carboxy-$C_{1-4}$alkyl.

An example of the present invention is a compound of Formula (I) and a form thereof wherein $R_2$ is selected from $C_{1-4}$alkyl, $C_{1-4}$alkoxy-$C_{1-4}$alkyl, $C_{1-4}$alkyl-thio-$C_{1-4}$alkyl, $C_{3-6}$cycloalkyl, $C_{3-6}$cycloalkyl-$C_{1-4}$alkyl, phenyl-$C_{1-4}$alkyl, heterocyclyl, heterocyclyl-$C_{1-4}$alkyl, heteroaryl-$C_{1-4}$alkyl or halo-$C_{1-4}$alkyl, wherein each instance of $C_{3-6}$cycloalkyl, heterocyclyl and heteroaryl is optionally substituted with $C_{1-4}$alkyl, phenyl or benzyl, wherein phenyl is optionally substituted with $C_{1-4}$alkyl, $C_{1-4}$alkoxy, amino, $C_{1-4}$alkyl-amino, hydroxy, cyano, halo-$C_{1-4}$alkyl or halogen.

An example of the present invention is a compound of Formula (I) and a form thereof wherein $R_2$ is selected from $C_{1-4}$alkyl, $C_{3-6}$cycloalkyl, heterocyclyl, heterocyclyl-$C_{1-4}$alkyl or heteroaryl-$C_{1-4}$alkyl, wherein each instance of $C_{3-6}$cycloalkyl, heterocyclyl and heteroaryl is optionally substituted with $C_{1-4}$alkyl, phenyl or benzyl, wherein phenyl is optionally substituted with halogen.

An example of the present invention is a compound of Formula (I) and a form thereof wherein $R_2$ is selected from $C_{1-4}$alkyl, cyclopropyl, heterocyclyl, pyrrolidinyl-$C_{1-4}$alkyl, tetrahydrofuranyl-$C_{1-4}$alkyl, furanyl-$C_{1-4}$alkyl, thienyl-$C_{1-4}$alkyl or pyrrolyl-$C_{1-4}$alkyl, wherein cyclopropyl is optionally substituted with phenyl, wherein phenyl is optionally substituted with halogen, and wherein pyrrolyl and pyrrolidinyl are each optionally substituted with $C_{1-4}$alkyl or benzyl.

An example of the present invention is a compound of Formula (I) and a form thereof wherein $R_2$ is selected from $C_{1-4}$alkyl, cyclopropyl, tetrahydrofuranyl-$C_{1-4}$alkyl or thienyl-$C_{1-4}$alkyl, wherein cyclopropyl is optionally substituted with phenyl, and wherein phenyl is optionally substituted with halogen.

An example of the present invention is a compound of Formula (I) and a form thereof wherein $R_2$ is cyclopropyl substituted with phenyl, wherein phenyl is optionally substituted with halogen.

An example of the present invention is a compound of Formula (I) and a form thereof wherein $R_2$ is cyclopropyl substituted with phenyl.

An example of the present invention is a compound of Formula (I) and a form thereof wherein $R_3$ and $R_4$ are each hydrogen.

An example of the present invention is a compound of Formula (I) and a form thereof wherein $R_3$ and $R_4$ are taken together with the carbon atoms of attachment to form a [1,3] dioxolanyl ring, wherein said ring is optionally substituted with one or two $C_{1-8}$alkyl substituents.

An example of the present invention is a compound of Formula (I) and a form thereof wherein $R_3$ and $R_4$ are taken together with the carbon atoms of attachment to form a [1,3] dioxolanyl ring, wherein said ring is substituted with two methyl substituents.

An example of the present invention is a compound of Formula (I) and a form thereof wherein $X_1$ and $X_2$ are each selected from $CH_2$ or $CH(OH)$.

An example of the present invention is a compound of Formula (I) and a form thereof wherein $X_1$ and $X_2$ are each CH and the dashed line represents a double bond.

An example of the present invention is a compound of Formula (I) and a form thereof wherein
$R_1$ is selected from hydrogen, hydroxy-$C_{1-8}$alkyl or carboxy-$C_{1-8}$alkyl;
$R_2$ is selected from $C_{1-4}$alkyl, $C_{1-4}$alkoxy-$C_{1-4}$alkyl, $C_{1-4}$alkyl-thio-$C_{1-4}$alkyl, $C_{3-6}$cycloalkyl, $C_{3-6}$cycloalkyl-$C_{1-4}$alkyl, phenyl-$C_{1-4}$alkyl, heterocyclyl, heterocyclyl-$C_{1-4}$alkyl, heteroaryl-$C_{1-4}$alkyl or halo-$C_{1-4}$alkyl,
wherein each instance of $C_{3-6}$cycloalkyl, heterocyclyl and heteroaryl is optionally substituted with $C_{1-4}$alkyl, phenyl or benzyl, wherein phenyl is optionally substituted with $C_{1-4}$alkyl, $C_{1-4}$alkoxy, amino, $C_{1-4}$alkyl-amino, hydroxy, cyano, halo-$C_{1-4}$alkyl or halogen;
$R_3$ and $R_4$ are each hydrogen; and
$X_1$ and $X_2$ are each selected from CH, $CH_2$ or CH(OH), wherein when either $X_1$ or $X_2$ is CH, then $X_1$ and $X_2$ must both be CH and the dashed line represents a double bond.

An example of the present invention is a compound of Formula (I) and a form thereof wherein
$R_1$ is selected from hydrogen, hydroxy-$C_{1-4}$alkyl or carboxy-$C_{1-4}$alkyl;
$R_2$ is selected from $C_{1-4}$alkyl, $C_{3-6}$cycloalkyl, heterocyclyl, heterocyclyl-$C_{1-4}$alkyl or heteroaryl-$C_{1-4}$alkyl,
wherein each instance of $C_{3-6}$cycloalkyl, heterocyclyl and heteroaryl is optionally substituted with $C_{1-4}$alkyl, phenyl or benzyl, wherein phenyl is optionally substituted with halogen;
$R_3$ and $R_4$ are each hydrogen; and
$X_1$ and $X_2$ are each selected from CH, $CH_2$ or CH(OH), wherein when either $X_1$ or $X_2$ is CH, then $X_1$ and $X_2$ must both be CH and the dashed line represents a double bond.

An example of the present invention is a compound of Formula (I) and a form thereof wherein
$R_1$ is selected from hydrogen, hydroxy-$C_{1-4}$alkyl or carboxy-$C_{1-4}$alkyl;
$R_2$ is selected from $C_{1-4}$alkyl, cyclopropyl, heterocyclyl, pyrrolidinyl-$C_{1-4}$alkyl, tetrahydrofuranyl-$C_{1-4}$alkyl, furanyl-$C_{1-4}$alkyl, thienyl-$C_{1-4}$alkyl or pyrrolyl-$C_{1-4}$alkyl,
wherein cyclopropyl is optionally substituted with phenyl, wherein phenyl is optionally substituted with halogen, and wherein pyrrolyl and pyrrolidinyl are each optionally substituted with $C_{1-4}$alkyl or benzyl;
$R_3$ and $R_4$ are each hydrogen; and
$X_1$ and $X_2$ are each selected from CH, $CH_2$ or CH(OH), wherein when either $X_1$ or $X_2$ is CH, then $X_1$ and $X_2$ must both be CH and the dashed line represents a double bond.

An example of the present invention is a compound of Formula (I) and a form thereof wherein
$R_1$ is selected from hydrogen or hydroxy-$C_{1-4}$alkyl;
$R_2$ is selected from $C_{1-4}$alkyl, cyclopropyl, tetrahydrofuranyl-$C_{1-4}$alkyl or thienyl-$C_{1-4}$alkyl, wherein cyclopropyl is optionally substituted with phenyl, wherein phenyl is optionally substituted with halogen;
$R_3$ and $R_4$ are each hydrogen; and
$X_1$ and $X_2$ are each selected from CH, $CH_2$ or CH(OH), wherein when either $X_1$ or $X_2$ is CH, then $X_1$ and $X_2$ must both be CH and the dashed line represents a double bond.

An example of the present invention is a compound of Formula (I) and a form thereof wherein
$R_1$ is selected from hydrogen or hydroxy-$C_{1-4}$alkyl;
$R_2$ is cyclopropyl substituted with phenyl, wherein phenyl is optionally substituted with halogen;
$R_3$ and $R_4$ are each hydrogen; and
$X_1$ and $X_2$ are each selected from CH, $CH_2$ or CH(OH), wherein when either $X_1$ or $X_2$ is CH, then $X_1$ and $X_2$ must both be CH and the dashed line represents a double bond.

An example of the present invention is a compound of Formula (I) and a form thereof wherein
$R_1$ is selected from hydrogen or hydroxy-$C_{1-4}$alkyl;
$R_2$ is cyclopropyl substituted with phenyl;
$R_3$ and $R_4$ are each hydrogen; and
$X_1$ and $X_2$ are each selected from CH, $CH_2$ or CH(OH), wherein when either $X_1$ or $X_2$ is CH, then $X_1$ and $X_2$ must both be CH and the dashed line represents a double bond.

An example of the present invention is a compound of Formula (I) and a form thereof wherein
$R_1$ is hydrogen or carboxy-$C_{1-4}$alkyl;
$R_2$ is selected from $C_{1-4}$alkyl, cyclopropyl, tetrahydrofuranyl-$C_{1-4}$alkyl or thienyl-$C_{1-4}$alkyl, wherein cyclopropyl is optionally substituted with phenyl, wherein phenyl is optionally substituted with halogen;
$R_3$ and $R_4$ are each hydrogen; and
$X_1$ and $X_2$ are each selected from CH, $CH_2$ or CH(OH), wherein when either $X_1$ or $X_2$ is CH, then $X_1$ and $X_2$ must both be CH and the dashed line represents a double bond.

An example of the present invention is a compound of Formula (I) and a form thereof wherein
$R_1$ is hydrogen or carboxy-$C_{1-4}$alkyl;
$R_2$ is cyclopropyl substituted with phenyl, wherein phenyl is optionally substituted with halogen;
$R_3$ and $R_4$ are each hydrogen; and
$X_1$ and $X_2$ are each selected from CH, $CH_2$ or CH(OH), wherein when either $X_1$ or $X_2$ is CH, then $X_1$ and $X_2$ must both be CH and the dashed line represents a double bond.

An example of the present invention is a compound of Formula (I) and a form thereof wherein
$R_1$ is hydrogen or carboxy-$C_{1-4}$alkyl;
$R_2$ is cyclopropyl substituted with phenyl;
$R_3$ and $R_4$ are each hydrogen; and
$X_1$ and $X_2$ are each selected from CH, $CH_2$ or CH(OH), wherein when either $X_1$ or $X_2$ is CH, then $X_1$ and $X_2$ must both be CH and the dashed line represents a double bond.

Compounds representative of a compound of Formula (I) or a form thereof include compounds and forms thereof selected from the group consisting of:

Cpd 1
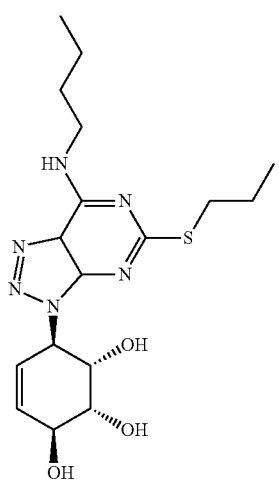
Cpd 4
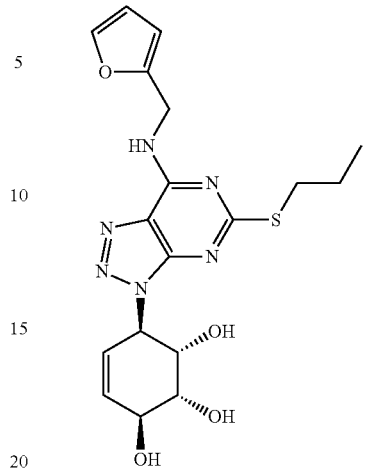
Cpd 2
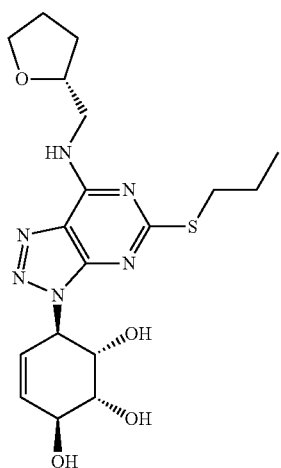
Cpd 5
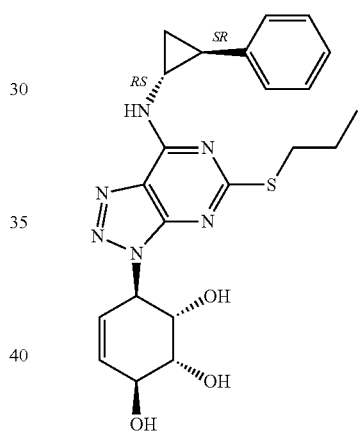
Cpd 3
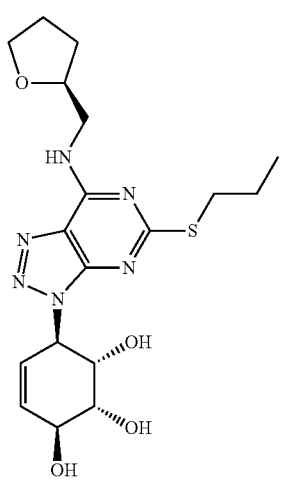
Cpd 6
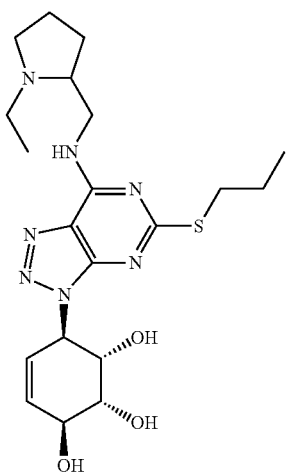

Cpd 7
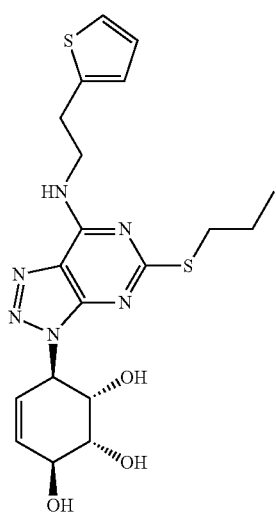
Cpd 8
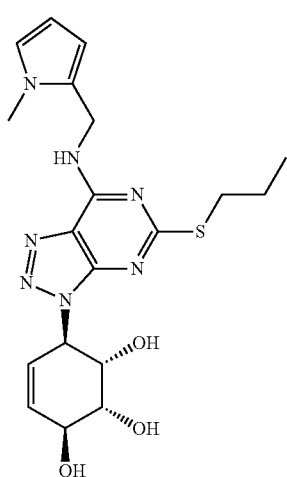
Cpd 9
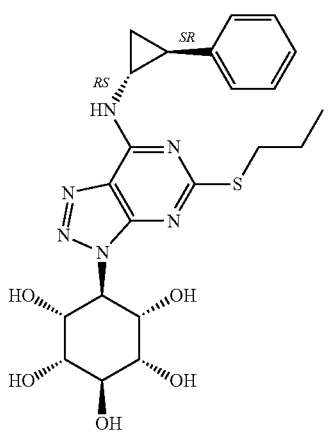
Cpd 10
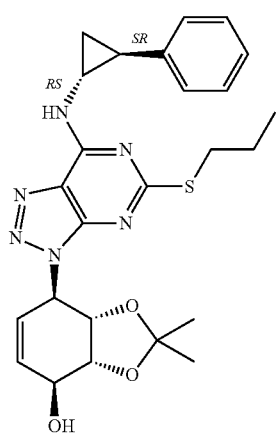
Cpd 11
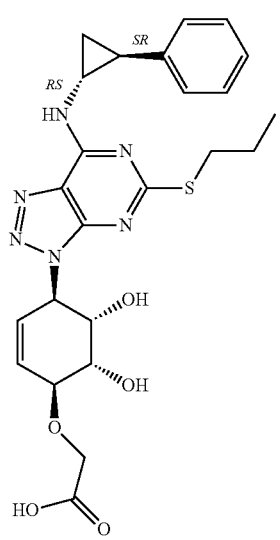
Cpd 12

Cpd 13
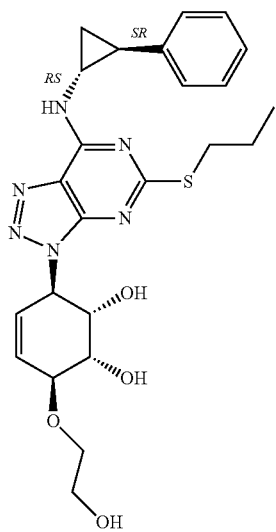
Cpd 14
Cpd 15
Cpd 16
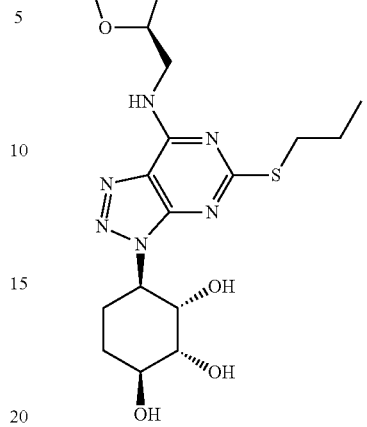
Cpd 17
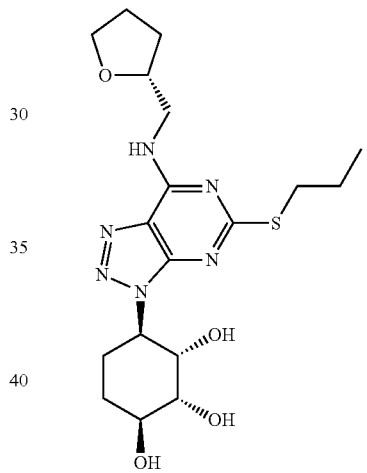
Cpd 18
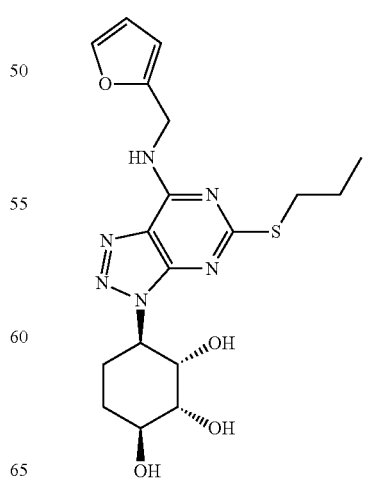

Cpd 19

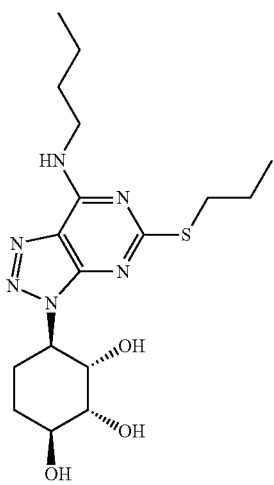

Cpd 20

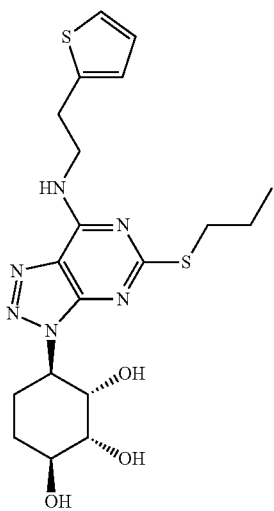

Cpd 21

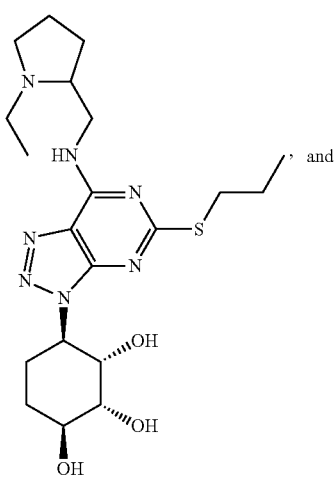, and

Cpd 22

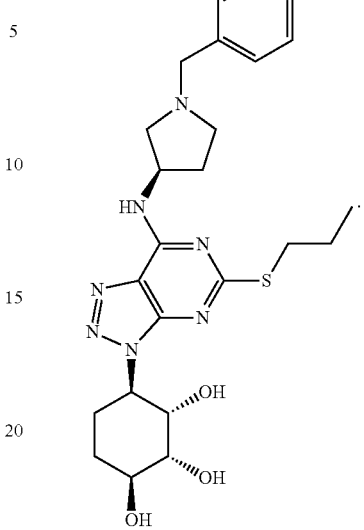

Compounds representative of a compound of Formula (I) or a form thereof include Compounds 1 to 22 and forms thereof selected from:

| Cpd | Name |
|---|---|
| 1 | (1S,2R,3S,6R)-6-(7-butylamino-5-propylsulfanyl-[1,2,3]triazolo[4,5-d]pyrimidin-3-yl)-cyclohex-4-ene-1,2,3-triol, |
| 2 | (1S,2R,3S,6R)-6-(5-propylsulfanyl-7-{[(2R)-tetrahydro-furan-2-ylmethyl]-amino}-[1,2,3]triazolo[4,5-d]pyrimidin-3-yl)-cyclohex-4-ene-1,2,3-triol, |
| 3 | (1S,2R,3S,6R)-6-(5-propylsulfanyl-7-{[(2S)-tetrahydro-furan-2-ylmethyl]-amino}-[1,2,3]triazolo[4,5-d]pyrimidin-3-yl)-cyclohex-4-ene-1,2,3-triol, |
| 4 | (1S,2R,3S,4R)-6-{7-[(furan-2-ylmethyl)-amino]-5-propylsulfanyl-[1,2,3]triazolo[4,5-d]pyrimidin-3-yl}-cyclohex-4-ene-1,2,3-triol, |
| 5 | (1S,2R,3S,6R)-6-{7-[(1RS,2SR)-2-phenyl-cyclopropyl-amino]-5-propylsulfanyl-[1,2,3]triazolo[4,5-d]pyrimidin-3-yl}-cyclohex-4-ene-1,2,3-triol, |
| 6 | (1S,2R,3S,4R)-6-{7-[(1-ethyl-pyrrolidin-2-ylmethyl)-amino]-5-propylsulfanyl-[1,2,3]triazolo[4,5-d]pyrimidin-3-yl}-cyclohex-4-ene-1,2,3-triol, |
| 7 | (1S,2R,3S,4R)-6-[5-propylsulfanyl-7-(2-thiophen-2-yl-ethylamino)-]1,2,3[triazolo]4,5-d[pyrimidin-3-yl]-cyclohex-4-ene-1,2,3-triol, |
| 8 | (1S,2R,3S,6R)-6-{7-[(1-methyl-1H-pyrrol-2-ylmethyl)-amino]-5-propylsulfanyl-[1,2,3]triazolo[4,5-d]pyrimidin-3-yl}-cyclohex-4-ene-1,2,3-triol, |
| 9 | (1R,2R,4S,5S)-6-{7-[(1RS,2SR)-phenyl-cyclopropyl-amino]-5-propylsulfanyl-[1,2,3]triazolo[4,5-d]pyrimidin-3-yl}-cyclohexane-1,2,3,4,5-pentaol, |
| 10 | (3aR,4S,7R,7aS)-2,2-dimethyl-7{7-[(1RS,2SR)-2-phenyl-cyclopropylamino]-5-propylsulfanyl-[1,2,3]triazolo[4,5-d]pyrimidin-3-yl}-3a,4,7,7a-tetrahydro-benzo[1,3]dioxol-4-ol, |
| 11 | [(1S,4R,5S,6S)-5,6-dihydroxy-4-{7-[(1RS,2SR)-2-phenyl-cyclopropylamino]-5-propylsulfanyl-[1,2,3]triazolo[4,5-d]pyrimidin-3-yl}-cyclohex-2-enyloxy]-acetic acid, |
| 12 | (1R,2R,4S,5S)-3-(2-hydroxy-ethoxy)-6-{7-[(1RS,2SR)-2-phenyl-cyclopropylamino]-5-propylsulfanyl-]1,2,3[triazolo]4,5-d[pyrimidin-3-yl}-cyclohexane-1,2,4,5-tetraol, |
| 13 | (1S,2S,3S,6R)-3-(2-hydroxy-ethoxy)-6-{7-[(1RS,2SR)-2-phenyl-cyclopropylamino]-5-propylsulfanyl-]1,2,3[triazolo]4,5-d[pyrimidin-3-yl}-cyclohex-4-ene-1,2-diol, |
| 14 | (1S,2R,3S,4R)-4-{7-[(1RS,2SR)-2-phenyl-cyclopropyl-amino]-5-propylsulfanyl-[1,2,3]triazolo[4,5-d]pyrimidin-3-yl}-cyclohexane-1,2,3-triol, |

| Cpd | Name |
|---|---|
| 15 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2-diol, |
| 16 | (1S,2R,3S,4R)-4-(5-propylsulfanyl-7-{[(2S)-tetrahydro-furan-2-ylmethyl]-amino}-[1,2,3]triazolo[4,5-d]pyrimidin-3-yl)-cyclohexane-1,2,3-triol, |
| 17 | (1S,2R,3S,4R)-4-(5-propylsulfanyl-7-{[(2R)-tetrahydro-furan-2-ylmethyl]-amino}-[1,2,3]triazolo[4,5-d]pyrimidin-3-yl)-cyclohexane-1,2,3-triol, |
| 18 | (1S,2R,3S,4R)-4-{7-[(furan-2-ylmethyl)-amino]-5-propylsulfanyl-[1,2,3]triazolo[4,5-d]pyrimidin-3-yl}-cyclohexane-1,2,3-triol, |
| 19 | (1S,2R,3S,4R)-4-(7-butylamino-5-propylsulfanyl-[1,2,3]triazolo[4,5-d]pyrimidin-3-yl)-cyclohexane-1,2,3-triol, |
| 20 | (1S,2R,3S,4R)-4-[5-propylsulfanyl-7-(2-thiophen-2-yl-ethylamino)-[1,2,3]triazolo[4,5-d]pyrimidin-3-yl]-cyclohexane-1,2,3-triol, |
| 21 | (1S,2R,3S,4R)-4-{7-[(1-ethyl-pyrrolidin-2-ylmethyl)-amino]-5-propylsulfanyl-[1,2,3]triazolo[4,5-d]pyrimidin-3-yl}-cyclohexane-1,2,3-triol, and |
| 22 | (1S,2R,3S,4R)-4-{7-[(3R)-1-benzyl-pyrrolidin-3-ylamino]-5-propylsulfanyl-[1,2,3]triazolo[4,5-d]pyrimidin-3-yl}-cyclohexane-1,2,3-triol. |

Compounds representative of a compound of Formula (I) or a form thereof include compounds and forms thereof selected from:

| Cpd | Name |
|---|---|
| 1 | (1S,2R,3S,6R)-6-(7-butylamino-5-propylsulfanyl-[1,2,3]triazolo[4,5-d]pyrimidin-3-yl)-cyclohex-4-ene-1,2,3-triol, |
| 3 | (1S,2R,3S,6R)-6-(5-propylsulfanyl-7-{[(2S)-tetrahydro-furan-2-ylmethyl]-amino}-[1,2,3]triazolo[4,5-d]pyrimidin-3-yl)-cyclohex-4-ene-1,2,3-triol, |
| 5 | (1S,2R,3S,6R)-6-{7-[(1RS,2SR)-2-phenyl-cyclopropyl-amino]-5-propylsulfanyl-[1,2,3]triazolo[4,5-d]pyrimidin-3-yl}-cyclohex-4-ene-1,2,3-triol, |
| 7 | (1S,2R,3S,4R)-6-[5-propylsulfanyl-7-(2-thiophen-2-yl-ethylamino)-[1,2,3]triazolo[4,5-d]pyrimidin-3-yl]-cyclohex-4-ene-1,2,3-triol, |
| 9 | (1R,2R,4S,5S)-6-{7-[(1RS,2SR)-phenyl-cyclopropyl-amino]-5-propylsulfanyl-[1,2,3]triazolo[4,5-d]pyrimidin-3-yl}-cyclohexane-1,2,3,4,5-pentaol, |
| 11 | [(1S,4R,5S,6S)-5,6-dihydroxy-4-{7-[(1RS,2SR)-2-phenyl-cyclopropylamino]-5-propylsulfanyl-[1,2,3]triazolo[4,5-d]pyrimidin-3-yl}-cyclohex-2-enyloxy]-acetic acid, |
| 12 | (1R,2R,4S,5S)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2,4,5-tetraol, |
| 13 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohex-4-ene-1,2-diol, |
| 14 | (1S,2R,3S,4R)-4-{7-[(1RS,2SR)-2-phenyl-cyclopropyl-amino]-5-propylsulfanyl-[1,2,3]triazolo[4,5-d]pyrimidin-3-yl}-cyclohexane-1,2,3-triol, |
| 15 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2-diol, and |
| 19 | (1S,2R,3S,4R)-4-(7-butylamino-5-propylsulfanyl-[1,2,3]triazolo[4,5-d]pyrimidin-3-yl)-cyclohexane-1,2,3-triol. |

Compounds representative of a compound of Formula (I) or a form thereof include compounds and forms thereof selected from:

| Cpd | Name |
|---|---|
| 1 | (1S,2R,3S,6R)-6-(7-butylamino-5-propylsulfanyl-[1,2,3]triazolo[4,5-d]pyrimidin-3-yl)-cyclohex-4-ene-1,2,3-triol, |
| 3 | (1S,2R,3S,6R)-6-(5-propylsulfanyl-7-{[(2S)-tetrahydro-furan-2-ylmethyl]-amino}-[1,2,3]triazolo[4,5-d]pyrimidin-3-yl)-cyclohex-4-ene-1,2,3-triol, |
| 5 | (1S,2R,3S,6R)-6-{7-[(1RS,2SR)-2-phenyl-cyclopropyl-amino]-5-propylsulfanyl-[1,2,3]triazolo[4,5-d]pyrimidin-3-yl}-cyclohex-4-ene-1,2,3-triol, |
| 7 | (1S,2R,3S,4R)-6-[5-propylsulfanyl-7-(2-thiophen-2-yl-ethylamino)-[1,2,3]triazolo[4,5-d]pyrimidin-3-yl]-cyclohex-4-ene-1,2,3-triol, |
| 9 | (1R,2R,4S,5S)-6-{7-[(1RS,2SR)-phenyl-cyclopropyl-amino]-5-propylsulfanyl-[1,2,3]triazolo[4,5-d]pyrimidin-3-yl}-cyclohexane-1,2,3,4,5-pentaol, |
| 11 | [(1S,4R,5S,6S)-5,6-dihydroxy-4-{7-[(1RS,2SR)-2-phenyl-cyclopropylamino]-5-propylsulfanyl-[1,2,3]triazolo[4,5-d]pyrimidin-3-yl}-cyclohex-2-enyloxy]-acetic acid, |
| 12 | (1R,2R,4S,5S)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2,4,5-tetraol, |
| 14 | (1S,2R,3S,4R)-4-{7-[(1RS,2SR)-2-phenyl-cyclopropyl-amino]-5-propylsulfanyl-[1,2,3]triazolo[4,5-d]pyrimidin-3-yl}-cyclohexane-1,2,3-triol, |
| 15 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2-diol, and |
| 19 | (1S,2R,3S,4R)-4-(7-butylamino-5-propylsulfanyl-[1,2,3]triazolo[4,5-d]pyrimidin-3-yl)-cyclohexane-1,2,3-triol. |

Compounds representative of a compound of Formula (I) or a form thereof include compounds and forms thereof selected from:

| Cpd | Name |
|---|---|
| 5 | (1S,2R,3S,6R)-6-{7-[(1RS,2SR)-2-phenyl-cyclopropyl-amino]-5-propylsulfanyl-[1,2,3]triazolo[4,5-d]pyrimidin-3-yl}-cyclohex-4-ene-1,2,3-triol, |
| 11 | [(1S,4R,5S,6S)-5,6-dihydroxy-4-{7-[(1RS,2SR)-2-phenyl-cyclopropylamino]-5-propylsulfanyl-[1,2,3]triazolo[4,5-d]pyrimidin-3-yl}-cyclohex-2-enyloxy]-acetic acid, and |
| 14 | (1S,2R,3S,4R)-4-{7-[(1RS,2SR)-2-phenyl-cyclopropyl-amino]-5-propylsulfanyl-[1,2,3]triazolo[4,5-d]pyrimidin-3-yl}-cyclohexane-1,2,3-triol. |

Compound Forms

The term "form" means a salt, stereoisomer, tautomer, crystalline state, polymorph, amorphous state, solvate, hydrate, ester, prodrug or metabolite of a compound of the present invention. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, 3$^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to a isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule which, in a given configuration, cannot be superimposed on its mirror image. This is in contrast to achiral molecules which can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration. In the "E" configuration, the substituents are on opposite sides in relationship to the carbon-carbon double bond. In the "Z" configuration, the substituents are oriented on the same side in relationship to the carbon-carbon double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

Chemical Definitions

As used herein, the following terms are intended to have the following meanings (additional definitions are provided where needed throughout the Specification). The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-8}$alkyl," whether used alone or as part of a substituent group, means a straight or branched chain hydrocarbon alkyl radical or alkyldiyl linking group, respectively, comprising from 1 to 8 carbon atoms, wherein the radical is derived by the removal of one hydrogen atom from a single carbon atom and the alkyldiyl linking group is derived by the removal of one hydrogen atom from each of two carbon atoms in the chain. Examples include methyl, ethyl, 1-propyl, 2-propyl, 1-butyl, 2-butyl, tertiary butyl, 1-pentyl, 2-pentyl, 3-pentyl, 1-hexyl, 2-hexyl, 3-hexyl and the like. Other examples include $C_{1-4}$alkyl groups. $C_{1-8}$alkyl is substituted on one or more available carbon chain atoms with one or more substituents when allowed by available valences.

The term "$C_{1-8}$alkoxy," whether used alone or as part of a substituent group, means a straight or branched chain hydrocarbon alkyl radical or alkyldiyl linking group of the formula —O—$C_{1-8}$alkyl, comprising from 1 to 8 carbon atoms, wherein the alkyldiyl linking group is derived by the removal of one hydrogen atom from a carbon atom in the chain. Examples include methoxy, ethoxy, propoxy and the like. Other examples include $C_{1-4}$alkoxy groups. $C_{1-8}$alkoxy is substituted on one or more available carbon chain atoms with one or more substituents when allowed by available valences.

The term "$C_{1-8}$alkoxy-$C_{1-8}$alkyl" means a radical of the formula: —$C_{1-8}$alkyl-O—$C_{1-8}$alkyl, wherein each $C_{1-8}$alkyl portion is optionally further substituted.

The term "$C_{1-8}$alkyl-thio-$C_{1-8}$alkyl" means a radical of the formula: —$C_{1-8}$alkyl-S—$C_{1-8}$alkyl, wherein each $C_{1-8}$alkyl portion is optionally further substituted.

The term "$C_{3-8}$cycloalkyl," whether used alone or as part of a substituent group, refers to a saturated or partially unsaturated, monocyclic or polycyclic hydrocarbon ring system radical derived by the removal of one hydrogen atom from a single ring carbon atom. Typical cycloalkyl radicals include cyclopropyl, cyclobutyl, cyclopentyl, cyclohexyl, cycloheptyl, cyclooctyl and the like. $C_{3-8}$cycloalkyl is substituted on one or more available ring carbon atoms with one or more substituents when allowed by available valences.

The term "hetero," when used as a prefix for a ring system, refers to the replacement of at least one carbon atom member in the ring system with a heteroatom selected from N, O, S, S(O), or $SO_2$. A hetero ring may have 1, 2, 3, or 4 carbon atom members replaced by a nitrogen atom. Alternatively, a ring may have 0, 1, 2, or 3 nitrogen atom members and 1 oxygen or sulfur atom member. Alternatively, up to two adjacent ring members may be heteroatoms, wherein one heteroatom is nitrogen and the other heteroatom is selected from N, S, or O.

The term "heterocyclyl" means a saturated or partially unsaturated monocyclic or polycyclic "hetero" ring system radical having a cycloalkyl ring as the core molecule. Heterocyclyl ring systems include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl and the like. The term "heterocyclyl" also includes a benzofused-heterocyclyl ring system radical and the like, such as indolinyl (also referred to as 2,3-dihydro-indolyl), benzo[1,3]dioxolyl (also referred to as 1,3-benzodioxolyl), 2,3-dihydro-1,4-benzodioxinyl, 2,3-dihydro-benzofuranyl, 1,2-dihydro-phthalazinyl and the like. Heterocyclyl radicals may be attached to a core molecule and further substituted on any atom when allowed by available valences.

The term "heteroaryl" means an aromatic monocyclic or polycyclic unsaturated heterocyclyl radical. Heteroaryl ring systems include furyl, thienyl, pyrrolyl, oxazolyl, thiazolyl, imidazolyl, pyrazolyl, isoxazolyl, isothiazolyl, oxadiazolyl, triazolyl, thiadiazolyl, tetrazolyl, pyridinyl, pyridazinyl, pyrimidinyl, pyrazinyl and the like. Heteroaryl radicals may be attached to a core molecule and further substituted on any atom when allowed by available valences.

The term "heteroaryl" also includes a benzofused-heteroaryl ring system radical and the like, such as indolizinyl, indolyl, azaindolyl, isoindolyl, benzo[b]furyl, benzo[b]thienyl, indazolyl, azaindazolyl, benzoimidazolyl, benzothiazolyl, benzooxazolyl, benzoisoxazolyl, benzothiadiazolyl, benzotriazolyl, purinyl, 4H-quinolizinyl, quinolinyl, isoquinolinyl, cinnolinyl, phthalzinyl, quinazolinyl, quinoxalinyl, 1,8-naphthyridinyl, pteridinyl and the like. Benzofused-heteroaryl radicals may be attached to a core molecule and further substituted on any atom when allowed by available valences.

The term "benzofused," when used as a prefix for a ring system, refers to a radical formed by any monocyclic radical fused with a benzene ring; the benzofused radical may be attached to a core molecule via either ring of the bicyclic system.

The term "$C_{3-8}$cycloalkyl-$C_{1-8}$alkyl" means a radical of the formula: —$C_{1-8}$alkyl-$C_{3-8}$cycloalkyl.

The term "heteroaryl-$C_{1-8}$alkyl" means a radical of the formula: —$C_{1-8}$alkyl-heteroaryl.

The term "heterocyclyl-$C_{1-8}$alkyl" means a radical of the formula: —$C_{1-8}$alkyl-heterocyclyl.

The term "phenyl-$C_{1-8}$alkyl" means a radical of the formula: —$C_{1-8}$alkyl-phenyl.

The term "halogen" or "halo" means the group chloro, bromo, fluoro or iodo.

The term "halo-$C_{1-8}$alkyl" means a radical of the formula: —$C_{1-8}$alkyl-halo, wherein $C_{1-8}$alkyl is substituted on one or more available carbon chain atoms with one or more halogen atoms when allowed by available valences.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

Therapeutic Use

The compounds of the present invention are useful as $P2_{12Y}$ inhibitors, having an $IC_{50}$ (50% inhibition concentration) in a range of about 25 μM or less, in a range of about 10 μM or less, in a range of about 1 μM or less, in a range of about 0.5 μM or less, or in a range of about 0.1 μM or less.

Accordingly, the present invention is further directed to a method for ameliorating, treating or preventing a platelet-mediated thrombotic disease, disorder or condition in a subject in need thereof comprising administering to the subject an effective amount of a compound of Formula (I) or a form thereof.

This invention is also directed to a method for inhibiting platelet aggregation in a subject in need thereof comprising administering to the subject an effective amount of a compound of Formula (I) or a form thereof.

Embodiments of the invention include the use of a compound of Formula (I) in the manufacture of a medicament for the treatment of the above disorders.

Embodiments of the method include the use of the compounds in therapy, especially adjunctive therapy, as inhibitors of platelet activation, aggregation and degranulation, promoters of platelet disaggregation, anti-thrombotic agents, or in the treatment or prophylaxsis of angina, unstable angina, coronary angioplasty, acute myocardial infarction (with or without thrombolysis), perithrombolysis, primary arterial thrombotic complications of atherosclerosis (such as thrombotic or embolic stroke, transient ischemic attacks or peripheral vascular disease), arterial complications due to interventions in atherosclerotic disease (such as angioplasty and reocclusion following angioplasty, endarterectomy, stent placement or coronary and other vascular graft surgery), thrombotic complications of surgical or mechanical damage (such as reocclusion following thrombolytic therapy, tissue salvage following accidental or surgical trauma or reconstructive surgery including skin and muscle flaps), conditions with a diffuse thrombotic/platelet consumption component (such as disseminated intravascular coagulation, thrombotic thrombocytopenic purpura, hemolytic uremic syndrome or thrombotic complications of septicemia), adult respiratory distress syndrome, anti-phospholipid syndrome, heparin-induced thrombocytopenia, pre-eclampsia/eclampsia, arterial thrombosis or venous thrombosis (such as deep vein thrombosis), venoocclusive disease, hematological conditions (such as myeloproliferative disease, including thrombocythemia or sickle cell disease); in the prevention of mechanically-induced platelet activation in vivo (such as cardio-pulmonary bypass and extracorporeal membrane oxygenation for the prevention of microthromboembolism), mechanically-induced platelet activation in vitro (such as use in the preservation of blood products, e.g. platelet concentrates), or shunt occlusion (such as in renal dialysis and plasmapheresis), thrombosis secondary to vascular damage/inflammation (such as vasculitis, arteritis, glomerulonephritis, inflammatory bowel disease and organ graft rejection), conditions such as migraine, Raynaud's phenomenon, conditions in which platelets can contribute to the underlying inflammatory disease process in the vascular wall (such as atheromatous plaque formation/progression or stenosis/restenosis) and in other inflammatory conditions (such as asthma, wherein platelets and platelet-derived factors are implicated in the immunological disease process).

Examples of the method include the use of the compounds of Formula (I) for treating acute myocardial infarction, primary arterial thrombotic complications of atherosclerosis (such as thrombotic or embolic stroke, transient ischemic attacks or peripheral vascular disease), arterial complications due to interventions in atherosclerotic disease (such as angioplasty and reocclusion following angioplasty), thrombotic complications of surgical or mechanical damage (such as reocclusion following thrombolytic therapy), arterial thrombosis, venous thrombosis, conditions in which platelets can contribute to the underlying inflammatory disease process in the vascular wall (such as atheromatous plaque formation/progression, stenosis/restenosis) and angina or unstable angina.

Examples of the method also include the use of the compounds of Formula (I) for treating arterial thrombosis, venous thrombosis, acute myocardial infarction, reocclusion following thrombolytic therapy, reocclusion following angioplasty, unstable angina and stroke.

The term "administering" with respect to the methods of the present invention, refers to a means for treating, ameliorating or preventing a disease as described herein with a compound specifically disclosed or a compound or prodrug thereof, which would obviously be included within the scope of the invention albeit not specifically disclosed for certain of the instant compounds.

Such methods include administering an effective amount of one or more compounds of Formula (I) or a form, composition or medicament thereof at different times during the course of a therapy or concurrently in a combination form. Such methods further include administering an effective amount of one or more compounds of Formula (I) or a form, composition or medicament thereof with one or more agents at different times during the course of a therapy or concurrently in a combination form.

The term "prodrug" refers to a metabolic precursor of a compound of Formula (I) or a form thereof. In general, a prodrug is a functional derivative of a compound which may be inactive when administered to a patient but is readily convertible in vivo into an active metabolite compound.

The term "active metabolite" refers to a metabolic product of a compound that is effective for ameliorating, treating or preventing a thrombin mediated disease, disorder or condition. Conventional procedures for the selection and preparation of suitable prodrug derivatives are described, for example, in "Design of Prodrugs", ed. H. Bundgaard, Elsevier, 1985.

The term "patient" as used herein, refers to an animal, preferably a mammal, most preferably a human, who has been the object of treatment, observation or experiment and is at risk of (or susceptible to) developing a disease or having a disease related to unregulated kinase activity.

The term "effective amount" refers to that amount of active compound or pharmaceutical agent that elicits the biological or medicinal response (such as inhibiting unregulated kinase activity) in a patient's tissue system, animal or human, that is being sought by a researcher, veterinarian, medical doctor, or other clinician.

The effective amount of a compound of Formula (I) exemplified in such a method is from about 0.001 mg/kg/day to about 300 mg/kg/day.

The term "composition" refers to a product containing one or more compounds of Formula (I) or a form thereof (such as a product comprising the specified ingredients in the specified amounts, as well as any product which results, directly or indirectly, from such combinations of the specified ingredients in the specified amounts).

The term "medicament" refers to one or more compounds of Formula (I) or a form thereof used in manufacturing a product for use in ameliorating, treating or preventing a thrombin mediated disease, disorder or condition.

A formulation of a composition or medicament of the present invention is "pharmaceutically acceptable" when the molecular entities and components used therein are of sufficient purity and quality such that, when appropriately administered to an animal or a human, the formulation does not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use.

Increased understanding of the mechanisms underlying thrombosis and of interventions therein has further led to a combination therapy approach using anti-platelet, anti-coagulant and fibrinolytic agents either singly or in combination as appropriate for use in either acute treatment or secondary prevention.

Examples of anti-thrombotic compounds used include antiplatelet agents such as aspirin, clopidogrel, ticlopidine, dipyridamole, GPIIb/IIIa antagonists, anti-coagulants (such as thrombin inhibitors, warfarin, factor Xa inhibitors, heparin and low molecular weight heparins) and fibrinolytic agents (such as streptokinase, tissue plasminogen activator and tenecteplase).

Thrombin inhibitors such as hirudin are highly effective antithrombotic agents, but again may produce excessive bleeding because they function as both anti-platelet and anti-coagulant agents.

The term "combination therapy" refers to the use of one or more compounds of Formula (I) or a form, composition or medicament thereof in combination with one or more anti-platelet, anti-coagulant or fibrinolytic agents either singly or in combination for ameliorating, treating or preventing a thrombin mediated disease, disorder or condition and advantageously may facilitate the use of a reduced effective dose of the compound of Formula (I) and/or the therapeutic agent than would be recommended for the treatment of a particular thrombin mediated disease, disorder or condition. Therefore, it is contemplated that the compounds of this invention can be used before, during or after treatment with a particular therapeutic agent.

Pharmaceutical Compositions

An embodiment of the present invention includes a composition comprising an admixture of one or more compounds of Formula (I) and/or one or more forms thereof and one or more excipients.

The forms for a compound of Formula (I) include a salt, ester, prodrug or active metabolite of a compound of Formula (I). The form for a compound of Formula (I) further includes a radio-labeled compound of Formula (I), whereby at least one hydrogen atom of the compound of Formula (I) is replaced with a deuterium or tritium atom. Other labeling techniques known to those skilled in the arts may also be used.

The present invention further includes the use of a process for making the composition or medicament comprising mixing one or more of the instant compounds and an optional carrier; and, includes those compositions or medicaments resulting from such a process. Contemplated processes include both conventional and unconventional pharmaceutical techniques.

The composition or medicament may take a wide variety of forms to effectuate mode of administration, including, but not limited to, intravenous (both bolus and infusion), oral, nasal, transdermal, topical with or without occlusion, and injection intraperitoneally, subcutaneously, intramuscularly, intratumorally or parenterally. The composition or medicament may be in a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation.

Compositions or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the composition or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing one or more compounds of Formula (I) or a form, composition or medicament thereof as an active ingredient contains an effective amount of the active ingredient necessary to be therapeutically or prophylactically effective.

The composition or medicament may contain from about 0.001 mg to about 5000 mg (preferably, from about 0.001 to about 500 mg) of active ingredient and may be constituted into any form suitable for the mode of administration selected for a patient in need.

A contemplated effective amount may range from about 0.001 mg to about 300 mg/kg of body weight per day. A contemplated effective amount may also range from about 0.003 to about 100 mg/kg of body weight per day. Another contemplated effective amount may range from about 0.1 to about 100 mg/kg of body weight per day. Another contemplated effective amount may also range from about 0.005 to about 15 mg/kg of body weight per day. The composition or medicament may be administered according to a dosage regimen of from about 1 to about 5 times per day.

For oral administration, the composition or medicament is preferably in the form of a tablet containing, e.g., 0.01, 0.05, 0.1, 0.5, 1.0, 2.5, 5.0, 10.0, 15.0, 25.0, 50.0, 100, 150, 200, 250, 500 milligrams and the like of the active ingredient for the symptomatic adjustment of the dosage to the patient to be treated. Optimal dosages will vary depending on factors associated with the particular patient being treated (e.g., age, weight, diet and time of administration), the severity of the condition being treated, the compound being employed, the mode of administration and the strength of the preparation. The use of either daily administration or post-periodic dosing may be employed.

A radio-labeled form of a compound of Formula (I), whereby at least one hydrogen atom of the compound of Formula (I) is replaced with a labeling atom such as a deuterium or tritium atom, may be used as a marker for the ADP receptor. Other labeling techniques known to those skilled in the arts may also be used.

Examples of the present invention further include methods for using a compound of Formula (I) or a form thereof in a pharmaceutical composition or medicament as described herein selected from the group consisting of:

| Cpd | Name |
|---|---|
| 1 | (1S,2R,3S,6R)-6-(7-butylamino-5-propylsulfanyl-[1,2,3]triazolo[4,5-d]pyrimidin-3-yl)-cyclohex-4-ene-1,2,3-triol, |
| 2 | (1S,2R,3S,6R)-6-(5-propylsulfanyl-7-{[(2R)-tetrahydro-furan-2-ylmethyl]-amino}-[1,2,3]triazolo[4,5-d]pyrimidin-3-yl)-cyclohex-4-ene-1,2,3-triol, |
| 3 | (1S,2R,3S,6R)-6-(5-propylsulfanyl-7-{[(2S)-tetrahydro-furan-2-ylmethyl]-amino}-[1,2,3]triazolo[4,5-d]pyrimidin-3-yl)-cyclohex-4-ene-1,2,3-triol, |
| 4 | (1S,2R,3S,4R)-6-{7-[(furan-2-ylmethyl)-amino]-5-propylsulfanyl-[1,2,3]triazolo[4,5-d]pyrimidin-3-yl}-cyclohex-4-ene-1,2,3-triol, |
| 5 | (1S,2R,3S,6R)-6-{7-[(1RS,2SR)-2-phenyl-cyclopropyl-amino]-5-propylsulfanyl-[1,2,3]triazolo[4,5-d]pyrimidin-3-yl}-cyclohex-4-ene-1,2,3-triol, |
| 6 | (1S,2R,3S,4R)-6-{7-[(1-ethyl-pyrrolidin-2-ylmethyl)-amino]-5-propylsulfanyl-[1,2,3]triazolo[4,5-d]pyrimidin-3-yl}-cyclohex-4-ene-1,2,3-triol, |

| Cpd | Name |
|---|---|
| 7 | (1S,2R,3S,4R)-6-[5-propylsulfanyl-7-(2-thiophen-2-yl-ethylamino)-[1,2,3]triazolo[4,5-d]pyrimidin-3-yl]-cyclohex-4-ene-1,2,3-triol, |
| 8 | (1S,2R,3S,6R)-6-{7-[(1-methyl-1H-pyrrol-2-ylmethyl)-amino]-5-propylsulfanyl-[1,2,3]triazolo[4,5-d]pyrimidin-3-yl}-cyclohex-4-ene-1,2,3-triol, |
| 9 | (1R,2R,4S,5S)-6-{7-[(1RS,2SR)-phenyl-cyclopropyl-amino]-5-propylsulfanyl-[1,2,3]triazolo[4,5-d]pyrimidin-3-yl}-cyclohexane-1,2,3,4,5-pentaol, |
| 10 | (3aR,4S,7R,7aS)-2,2-dimethyl-7-{7[(1RS,2SR)-phenyl-cyclopropylamino]-5-propylsulfanyl-[1,2,3]triazolo[4,5-d]pyrimidin-3-yl}-3a,4,7,7a-tetrahydro-benzo[1,3]dioxol-4-ol, |
| 11 | [(1S,4R,5S,6S)-5,6-dihydroxy-4-{7-[(1RS,2SR)-2-phenyl-cyclopropylamino]-5-propylsulfanyl-[1,2,3]triazolo[4,5-d]pyrimidin-3-yl}-cyclohex-2-enyloxy]-acetic acid, |
| 12 | (1R,2R,4S,5S)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2,4,5-tetraol, |
| 13 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohex-4-ene-1,2-diol, |
| 14 | (1S,2R,3S,4R)-4-{7-[(1RS,2SR)-2-phenyl-cyclopropyl-amino]-5-propylsulfanyl-[1,2,3]triazolo[4,5-d]pyrimidin-3-yl}-cyclohexane-1,2,3-triol, |
| 15 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2-diol, |
| 16 | (1S,2R,3S,4R)-4-(5-propylsulfanyl-7-{[(2S)-tetrahydro-furan-2-ylmethyl]-amino}-[1,2,3]triazolo[4,5-d]pyrimidin-3-yl)-cyclohexane-1,2,3-triol, |
| 17 | (1S,2R,3S,4R)-4-(5-propylsulfanyl-7-{[(2R)-tetrahydro-furan-2-ylmethyl]-amino}-[1,2,3]triazolo[4,5-d]pyrimidin-3-yl)-cyclohexane-1,2,3-triol, |
| 18 | (1S,2R,3S,4R)-4-{7-[(furan-2-ylmethyl)-amino]-5-propylsulfanyl-[1,2,3]triazolo[4,5-d]pyrimidin-3-yl}-cyclohexane-1,2,3-triol, |
| 19 | (1S,2R,3S,4R)-4-(7-butylamino-5-propylsulfanyl-[1,2,3]triazolo[4,5-d]pyrimidin-3-yl)-cyclohexane-1,2,3-triol, |
| 20 | (1S,2R,3S,4R)-4-[5-propylsulfanyl-7-(2-thiophen-2-yl-ethylamino)-[1,2,3]triazolo[4,5-d]pyrimidin-3-yl]-cyclohexane-1,2,3-triol, |
| 21 | (1S,2R,3S,4R)-4-{7-[(1-ethyl-pyrrolidin-2-ylmethyl)-amino]-5-propylsulfanyl-[1,2,3]triazolo[4,5-d]pyrimidin-3-yl}-cyclohexane-1,2,3-triol, and |
| 22 | (1S,2R,3S,4R)-4-{7-[(3R)-1-benzyl-pyrrolidin-3-ylamino]-5-propylsulfanyl-[1,2,3]triazolo[4,5-d]pyrimidin-3-yl}-cyclohexane-1,2,3-triol. |

Examples of the present invention further include methods for using a compound of Formula (I) or a form thereof in a pharmaceutical composition or medicament as described herein selected from the group consisting of:

| Cpd | Name |
|---|---|
| 1 | (1S,2R,3S,6R)-6-(7-butylamino-5-propylsulfanyl-[1,2,3]triazolo[4,5-d]pyrimidin-3-yl)-cyclohex-4-ene-1,2,3-triol, |
| 3 | (1S,2R,3S,6R)-6-(5-propylsulfanyl-7-{[(2S)-tetrahydro-furan-2-ylmethyl]-amino}-[1,2,3]triazolo[4,5-d]pyrimidin-3-yl)-cyclohex-4-ene-1,2,3-triol, |
| 5 | (1S,2R,3S,6R)-6-{7-[(1RS,2SR)-2-phenyl-cyclopropyl-amino]-5-propylsulfanyl-[1,2,3]triazolo[4,5-d]pyrimidin-3-yl}-cyclohex-4-ene-1,2,3-triol, |
| 7 | (1S,2R,3S,4R)-6-[5-propylsulfanyl-7-(2-thiophen-2-yl-ethylamino)-[1,2,3]triazolo[4,5-d]pyrimidin-3-yl]-cyclohex-4-ene-1,2,3-triol, |
| 9 | (1R,2R,4S,5S)-6-{7-[(1RS,2SR)-phenyl-cyclopropyl-amino]-5-propylsulfanyl-[1,2,3]triazolo[4,5-d]pyrimidin-3-yl}-cyclohexane-1,2,3,4,5-pentaol, |
| 11 | [(1S,4R,5S,6S)-5,6-dihydroxy-4-{7-[(1RS,2SR)-2-phenyl-cyclopropylamino]-5-propylsulfanyl-[1,2,3]triazolo[4,5-d]pyrimidin-3-yl}-cyclohex-2-enyloxy]-acetic acid, |
| 12 | (1R,2R,4S,5S)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2,4,5-tetraol, |
| 13 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohex-4-ene-1,2-diol, |
| 14 | (1S,2R,3S,4R)-4-{7-[(1RS,2SR)-2-phenyl-cyclopropyl-amino]-5-propylsulfanyl-[1,2,3]triazolo[4,5-d]pyrimidin-3-yl}-cyclohexane-1,2,3-triol, |
| 15 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2-diol, and |
| 19 | (1S,2R,3S,4R)-4-(7-butylamino-5-propylsulfanyl-[1,2,3]triazolo[4,5-d]pyrimidin-3-yl)-cyclohexane-1,2,3-triol. |

Examples of the present invention further include methods for using a compound of Formula (I) or a form thereof in a pharmaceutical composition or medicament as described herein selected from the group consisting of:

| Cpd | Name |
|---|---|
| 1 | (1S,2R,3S,6R)-6-(7-butylamino-5-propylsulfanyl-[1,2,3]triazolo[4,5-d]pyrimidin-3-yl)-cyclohex-4-ene-1,2,3-triol, |
| 3 | (1S,2R,3S,6R)-6-(5-propylsulfanyl-7-{[(2S)-tetrahydro-furan-2-ylmethyl]-amino}-[1,2,3]triazolo[4,5-d]pyrimidin-3-yl)-cyclohex-4-ene-1,2,3-triol, |
| 5 | (1S,2R,3S,6R)-6-{7-[(1RS,2SR)-2-phenyl-cyclopropyl-amino]-5-propylsulfanyl-[1,2,3]triazolo[4,5-d]pyrimidin-3-yl}-cyclohex-4-ene-1,2,3-triol, |
| 7 | (1S,2R,3S,4R)-6-[5-propylsulfanyl-7-(2-thiophen-2-yl-ethylamino)-[1,2,3]triazolo[4,5-d]pyrimidin-3-yl]-cyclohex-4-ene-1,2,3-triol, |
| 9 | (1R,2R,4S,5S)-6-{7-[(1RS,2SR)-phenyl-cyclopropyl-amino]-5-propylsulfanyl-[1,2,3]triazolo[4,5-d]pyrimidin-3-yl}-cyclohexane-1,2,3,4,5-pentaol, |
| 11 | [(1S,4R,5S,6S)-5,6-dihydroxy-4-{7-[(1RS,2SR)-2-phenyl-cyclopropylamino]-5-propylsulfanyl-[1,2,3]triazolo[4,5-d]pyrimidin-3-yl}-cyclohex-2-enyloxy]-acetic acid, |
| 12 | (1R,2R,4S,5S)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2,4,5-tetraol, |
| 14 | (1S,2R,3S,4R)-4-{7-[(1RS,2SR)-2-phenyl-cyclopropyl-amino]-5-propylsulfanyl-[1,2,3]triazolo[4,5-d]pyrimidin-3-yl}-cyclohexane-1,2,3-triol, |
| 15 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2-diol, and |
| 19 | (1S,2R,3S,4R)-4-(7-butylamino-5-propylsulfanyl-[1,2,3]triazolo[4,5-d]pyrimidin-3-yl)-cyclohexane-1,2,3-triol. |

Examples of the present invention further include methods for using a compound of Formula (I) or a form thereof in a pharmaceutical composition or medicament as described herein selected from the group consisting of:

| Cpd | Name |
|---|---|
| 5 | (1S,2R,3S,6R)-6-{7-[(1RS,2SR)-2-phenyl-cyclopropyl-amino]-5-propylsulfanyl-[1,2,3]triazolo[4,5-d]pyrimidin-3-yl}-cyclohex-4-ene-1,2,3-triol, |
| 11 | [(1S,4R,5S,6S)-5,6-dihydroxy-4-{7-[(1RS,2SR)-2-phenyl-cyclopropylamino]-5-propylsulfanyl-[1,2,3]triazolo[4,5-d]pyrimidin-3-yl}-cyclohex-2-enyloxy]-acetic acid, and |
| 14 | (1S,2R,3S,4R)-4-{7-[(1RS,2SR)-2-phenyl-cyclopropyl-amino]-5-propylsulfanyl-[1,2,3]triazolo[4,5-d]pyrimidin-3-yl}-cyclohexane-1,2,3-triol. |

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

The terms used in describing the invention are commonly used and known to those skilled in the art. When used herein, the following abbreviations or formulas have the indicated meanings:

| Abbreviation | Meaning |
| --- | --- |
| BSA | Bovine Serum Albumin |
| Cpd | compound |
| DCC | 1,3-dicyclohexylcarbodiimide |
| DCM | dichloromethane |
| DIEA | diisopropylethylamine |
| DMEM | Dulbecco's Modified Eagle Medium |
| DMF | N,N-dimethyl formamide |
| DMSO | dimethylsulfoxide |
| EtOAc | ethyl acetate |
| FBS | Fetal Bovine Serum |
| HOAc | acetic acid |
| HOBt | 1-hydroxybenzotriazole |
| KOH | potassium hydroxide |
| MeOH | methanol |
| min/h/hr | minute/hour |
| RT/R.T./rt/r.t. | room temperature |
| TFA | trifluoroacetic acid |
| THF | tetrahydrofuran |

General Synthetic Methods

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

Scheme A

Scheme A describes the preparation of certain intermediates and compounds of the present invention.

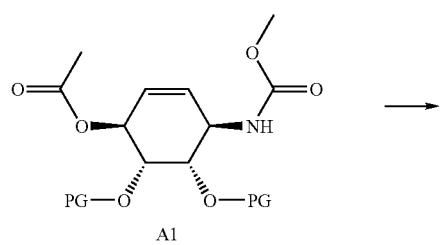

A1

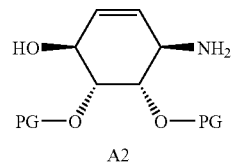

A2

A compound of formula A1 may be commercially available or may be made by those skilled in the art using conventional methods and known materials. A compound of formula A1 (wherein PG is a suitable hydroxyl protecting group) may be treated with a base (such as Ba(OH)$_2$) to afford a compound of formula A2.

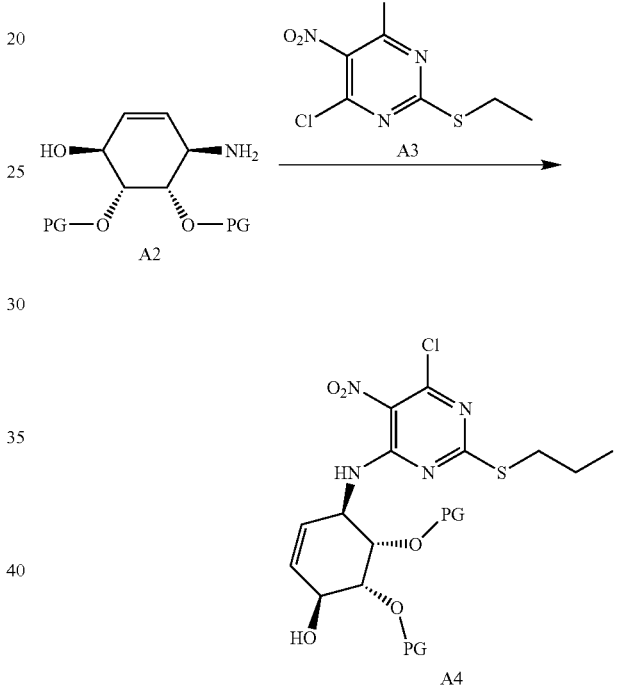

Reaction of the compound of formula A2 with a compound of formula A3 (prepared according to WO 99/05142) in the presence of a base (such as DIEA), affords a compound of formula A4.

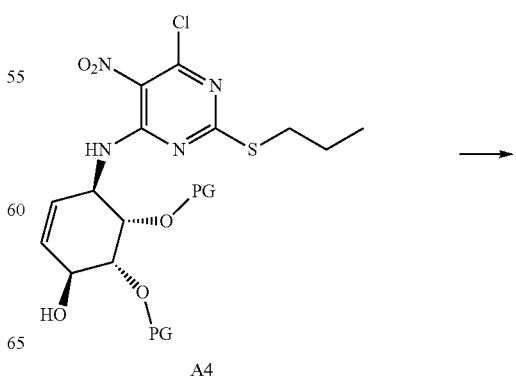

A4

-continued

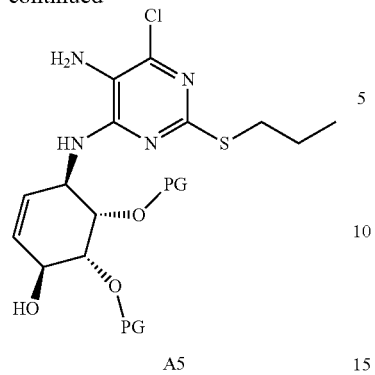

A5

The compound of formula A4 may be treated with a reducing agent (such as Fe) to give a compound of formula A5.

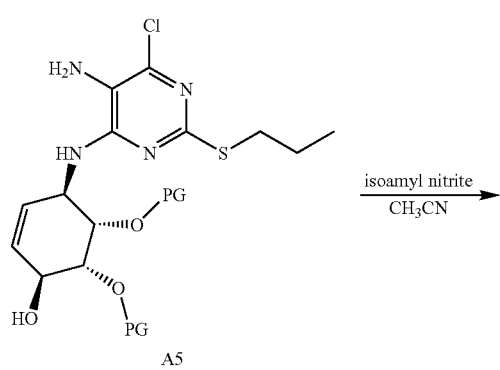

A5

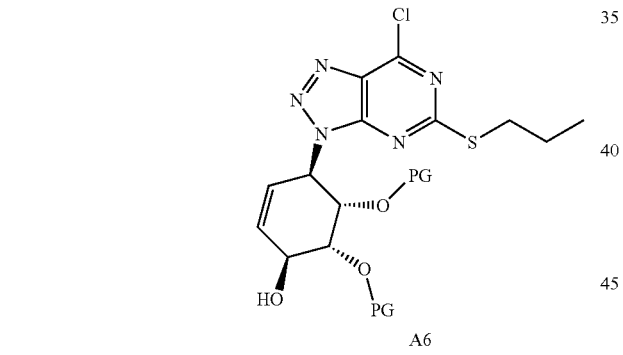

A6

Cyclization of the compound of formula A5 with isoamyl nitrite affords a compound of formula A6.

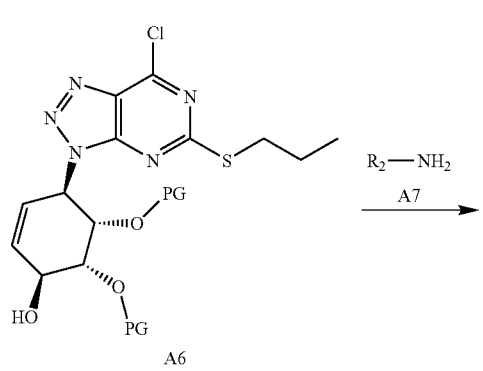

A6

-continued

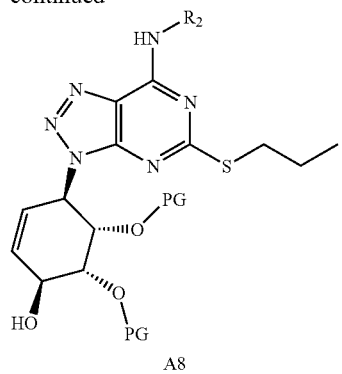

A8

Treatment of the compound of formula A6 with a substituted amine compound of formula A7 in the presence of a base (such as DIEA) provides a compound of formula A8.

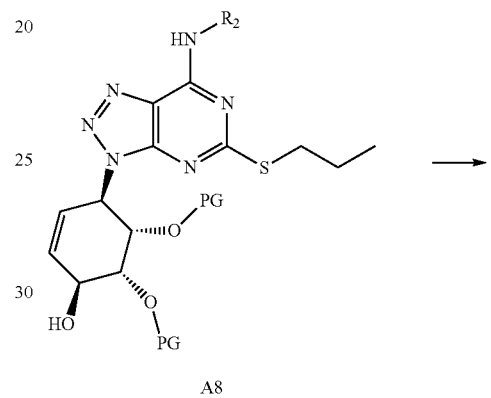

A8

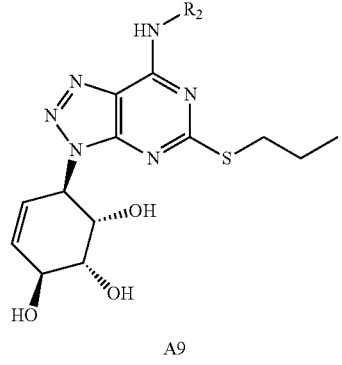

A9

Deprotection of the hydroxyl protecting groups on the compound of formula A8 affords the target compound of formula A9, representative of a compound of Formula (I).

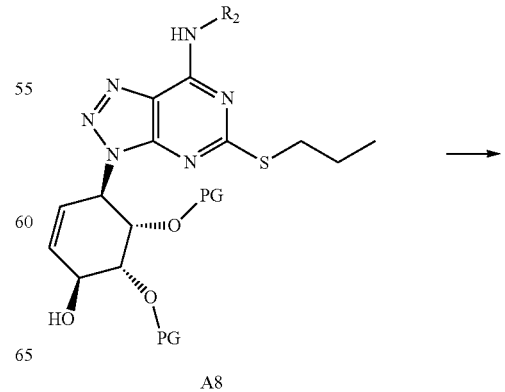

A8

-continued

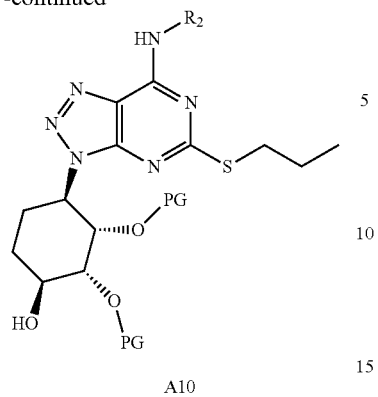

A10

The compound of formula A8 may also be treated with a reducing agent, such as $H_2$ in the presence of Pd/C, to give a saturated compound of formula A10.

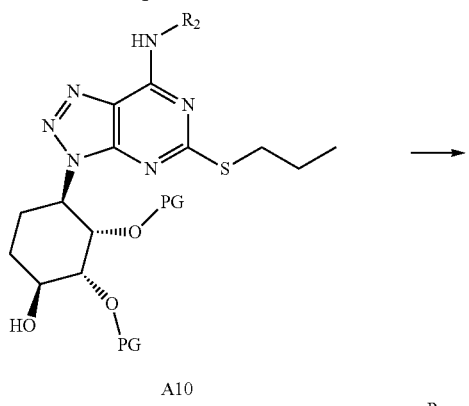

A10

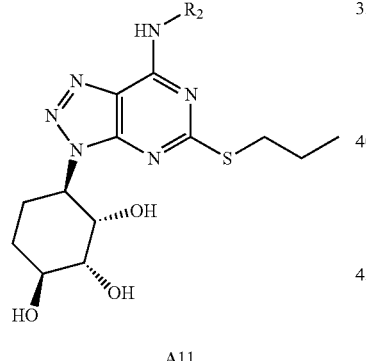

A11

Deprotection of the hydroxyl protecting groups on the compound of formula A10 affords a compound of formula A11, representative of a compound of Formula (I).

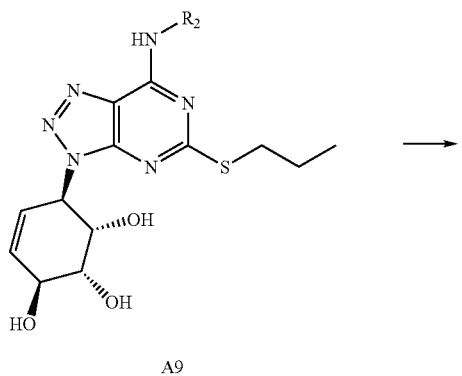

A9

-continued

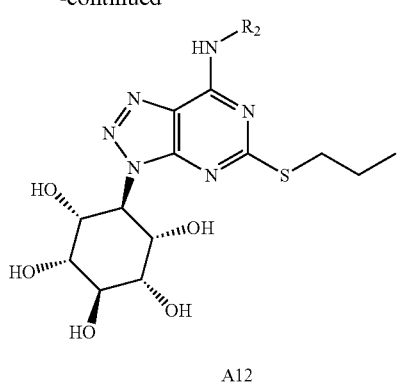

A12

Treatment of the compound of formula A9 with an oxidizing agent, such as 4-methylmorpholine-N-oxide/osmium tetroxide, affords a compound of formula A12, representative of a compound of Formula (I).

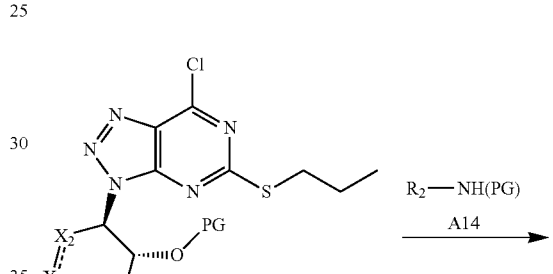

A13

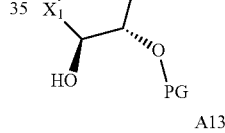

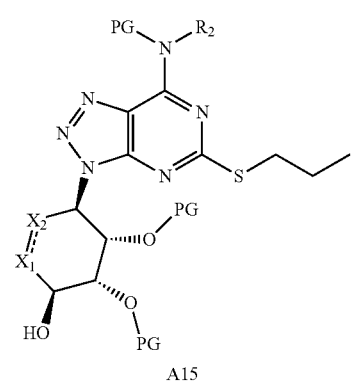

A15

Treatment of a compound of formula A13 (wherein $X_1$ and $X_2$ are each selected from CH or $CH_2$, wherein when either $X_1$ or $X_2$ is CH, then $X_1$ and $X_2$ must both be CH and the dashed line represents a double bond) with a protected substituted amine compound of formula A14 in the presence of a base (such as DIEA) provides a compound of formula A15.

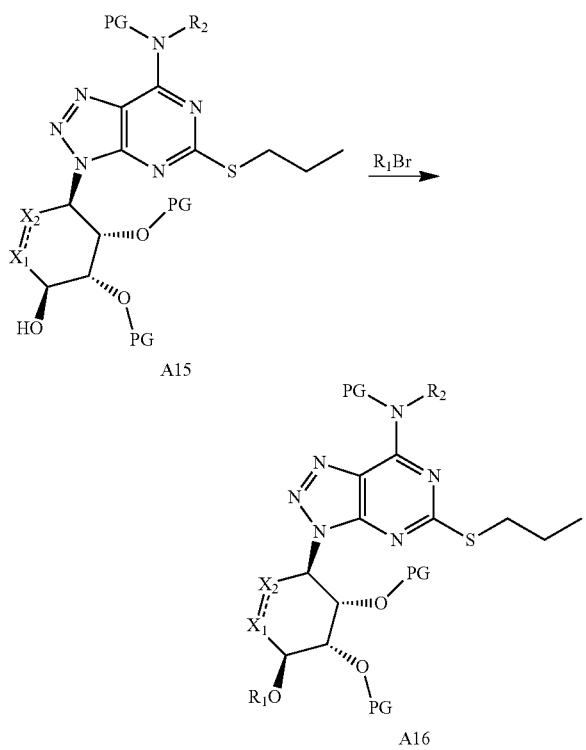

A15

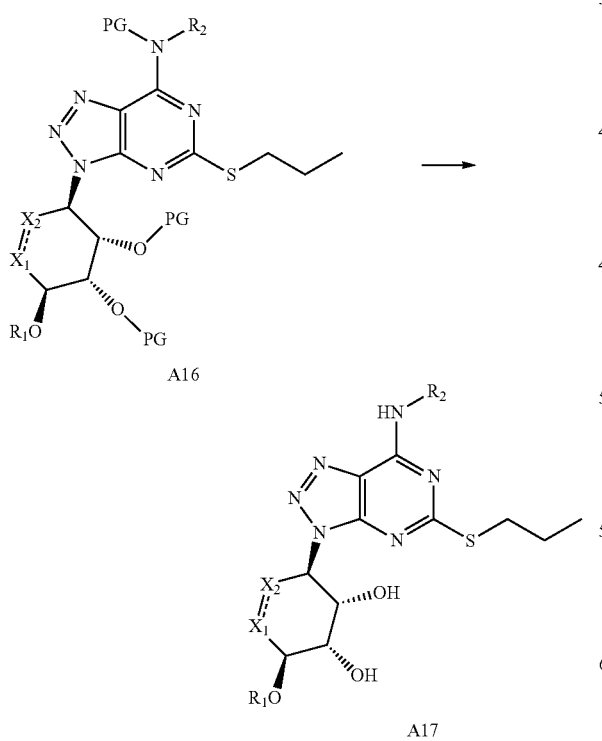

A16

The compound of formula A15 may be treated with an alkylating agent, such as R₁Br, in the presence of a base, to give a compound of formula A16.

A16

A17

Deprotection of both hydroxyl and nitrogen protecting groups on the compound of formula A16 affords a compound of formula A17, representative of a compound of Formula (I).

SPECIFIC SYNTHETIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

General: $^1$H and $^{13}$C NMR spectra were obtained at 400 MHz and 300 MHz on a Brucker AVANCE300 and AVANCE400 spectrometer. Chemical shifts are reported in ppm downfield from TMS as an internal standard. Magnesium sulfate was employed to dry organic extracts prior to concentration by rotary evaporation. Flash chromatography was done using EM science silica gel 60 (230-400 mesh). Standard solvents from J. T. Baker were used as received. Anhydrous solvents from Aldrich or J. T. Baker and all other commercially available reagents were used without further purification. Silica gel (E. Merck, 230-400 mesh) was used for all flash chromatography. Thin-layer chromatography was performed on precoated plates with silica gel 60 F254 from EM Science. Yields were not optimized. Mass electrospray positive or negative spectra (MS) was performed on Hewlett Packard 1100 series or Agilent 1100 series spectrometer with a Zorbax stablebond C18 narrow bore column, using gradient 0.05% acetic acid in methanol and 0.05% acetic acid in water as mobile phase for MS analysis, and using gradient 0.05% TFA in acetonitrile and 0.05% acetic acid in water as mobile phase for LCMS analysis. HPLC quantitative purity analysis were additionally carried on Agilent 1100 Series LC/MSD equipment on a Agilent 4.6×50 mm Zorbax 3.5 uM column (Elips XDB-phenyl) using gradient 0.05% TFA acetonitrile and 0.05% TFA in water as solvent system and based on the absorption at 254 nM.

Example 1

(1S,2R,3S,6R)-6-{7-[(1RS,2SR)-2-phenyl-cyclopropylamino]-5-propylsulfanyl-[1,2,3]triazolo[4,5-d]pyrimidin-3-yl}-cyclohex-4-ene-1,2,3-triol (Compound 5)

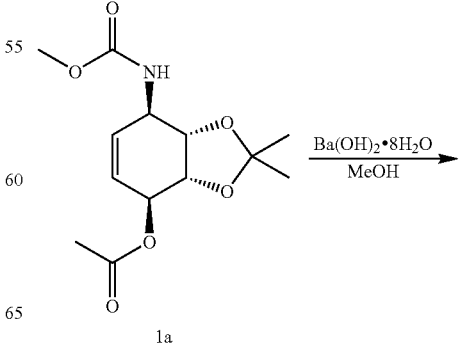

1a

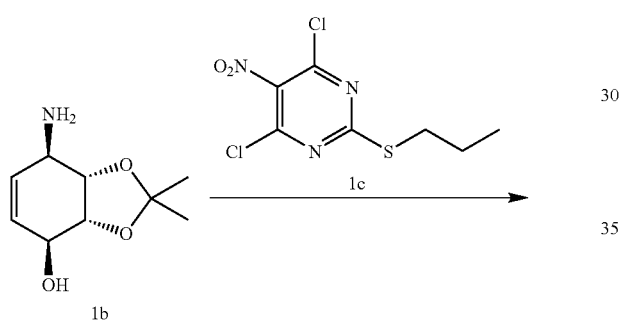

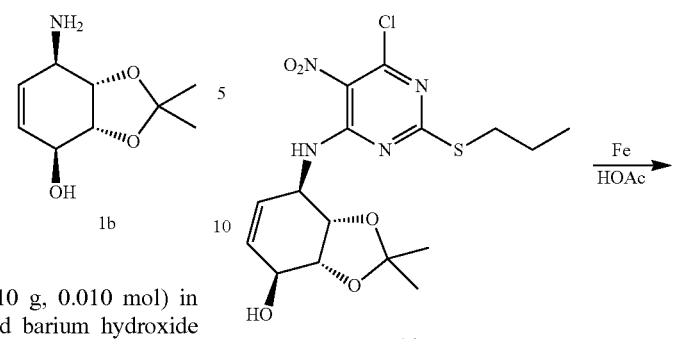

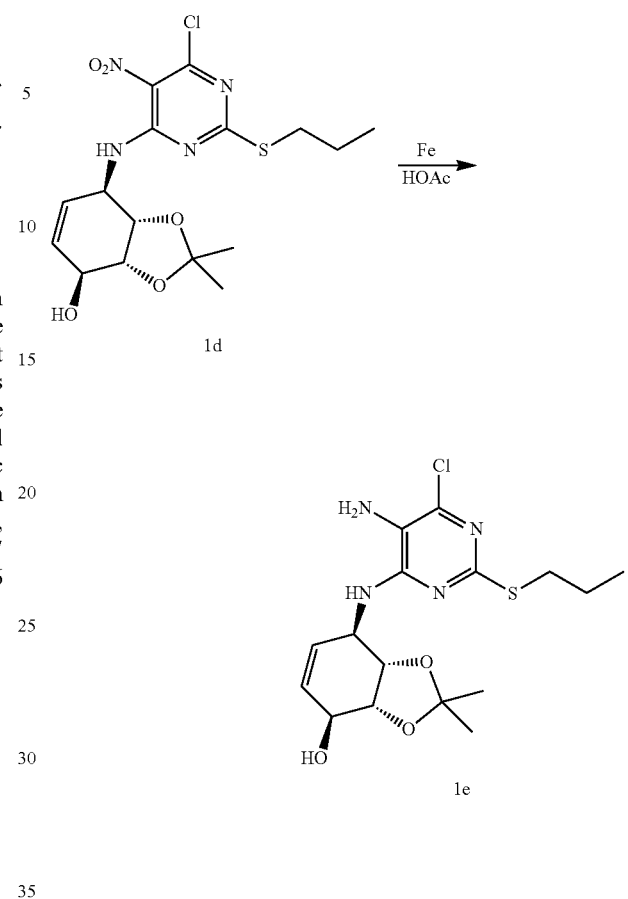

To a solution of compound 1a (4.10 g, 0.010 mol) in MeOH/H$_2$O (1:2, 150 mL) was added barium hydroxide octahydrate (10.0 g, 0.032 mol). The mixture was heated at 110° C. for 8 h, then 100° C. overnight. The white solid was then filtered out and washed with MeOH several times. The filtrate was evaporated and the residue was dissolved in small amount of H$_2$O and extracted with ethyl acetate. The organic layers were combined, dried (Na$_2$SO$_4$) and evaporated in vacuo to give 1b (2.39 g). $^1$H NMR (CDCl$_3$) δ 6.14 (m, 1H), 5.94 (m, 1H), 4.41 (dd, J=3.8, 7.5 Hz, 1H), 4.15 (m, 2H), 3.57 (t, J=4.2 Hz, 1H), 1.41 (s, 3H), 1.34 (s, 3H). ES-MS m/z 186 (MH$^+$).

To a solution of compound 1b (0.65 g, 3.53 mmol) in THF (20 mL) was added 1c (1.37 g, 5.12 mmol, prepared according to WO 99/05142), followed by DIEA (1.37 g, 10.6 mmol). The mixture was heated at 40° C. overnight. The solvent was evaporated and the crude product was purified via flash column chromatography (EtOAc/heptane, 1:3) to afford Compound 1d (0.87 g, 41%). $^1$H NMR (CDCl$_3$) δ 6.11 (m, 1H), 5.89 (m, 1H), 4.91 (m, 1H), 4.33 (m, 3H), 3.07 (t, J=7.3 Hz, 2H), 2.29 (m, 1H), 1.75 (m, 2H), 1.45 (s, 3H), 1.35 (s, 3H), 1.03 (t, J=7.3 Hz, 3H). ES-MS m/z 417 (MH$^+$).

To a solution of compound 1d (0.87 g, 2.09 mmol) in HOAc (15 mL) was added Fe (3.0 g, 54 mmol). The mixture was stirred at room temperature for 1 h. Then additional Fe (0.5 g, 8.95 mmol) was added and stirred at room temperature for another hour. Ethyl acetate and water were added to the reaction mixture. The aqueous layer was extracted several times with EtOAc. The combined EtOAc extracts were washed with water, brine and dried (Na$_2$SO$_4$) and concentrated to give the crude product 1e (0.95 g), which was used for the next step without further purification. $^1$H NMR (CD$_3$OD) δ 5.84 (m, 1H), 5.71 (m, 1H), 4.65 (dd, J=2.4, 6.2 Hz, 1H), 4.32 (m, 1H), 4.22 (m, 1H), 4.14 (m, 1H), 2.98 (m, 2H), 1.71 (m, 2H), 1.46 (s, 3H), 1.36 (s, 3H), 1.00 (t, J=7.3 Hz, 3H). ES-MS m/z 387 (MH$^+$).

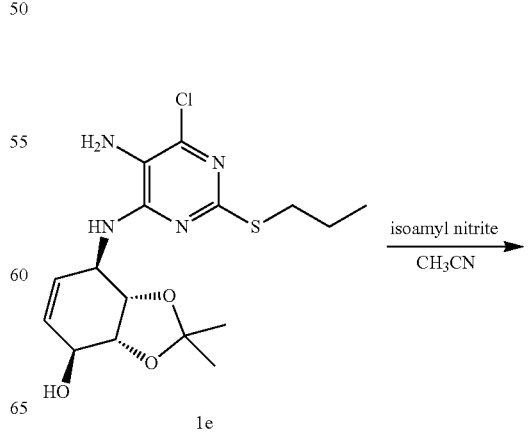

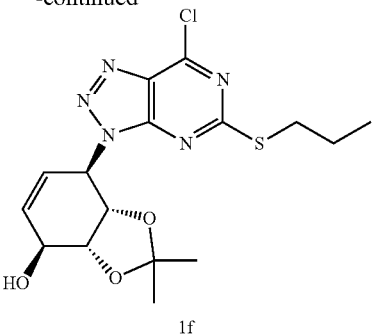

1f

To a mixture of Compound 1e (1.82 g, 4.7 mmol) in acetonitrile (40 mL) was added 96% isoamyl nitrite (0.98 mL, 7.06 mmol). The mixture was heated to 70° C. under Ar for 1 h. The solvent was evaporated and purified via flash chromatography (DCM/MeOH: 97:3) to afford Compound 1f (1.47 g, 79%). $^1$H NMR (CDCl$_3$) δ 6.15 (m, 1H), 5.90 (m, 1H), 5.43 (m, 1H), 4.72 (t, J=6.9 Hz, 1H), 4.48 (m, 1H), 4.40 (m, 1H), 3.17 (m, 2H), 1.81 (m, 2H), 1.55 (s, 3H), 1.53 (s, 3H), 1.07 (t, J=7.3 Hz, 3H). ES-MS m/z 398 (MH$^+$).

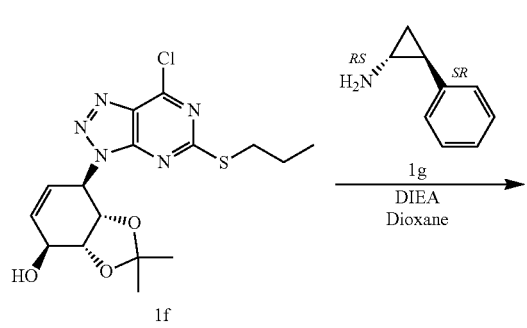

1f

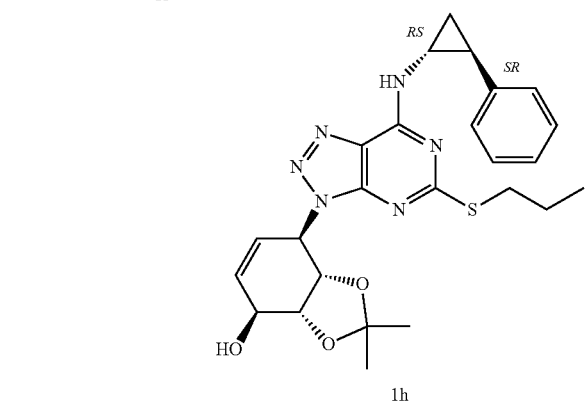

1h

To a mixture of compound 1f (0.46 g, 1.16 mmol) in 1,4-dioxane (10 mL) was added trans-2-phenylcyclopropylamine hydrochloride 1 g (0.39 g, 2.30 mmol) followed by addition of DIEA (0.6 mL). The mixture was stirred at rt for 5 h, then diluted with ethyl acetate and water. The organic layer was separated, washed with water, dried (Na$_2$SO$_4$) and concentrated to give crude product. The crude product was purified by flash chromatography (CH$_2$Cl$_2$/MeOH/NH$_4$OH: 97:3:0.3) to give Compound 1h (0.51 g, 89%). $^1$H NMR (CDCl$_3$) δ 7.26 (m, 5H), 6.54 (m, 1H), 6.20 (m, 1H), 5.86 (m, 1H), 5.43 (m, 1H), 4.71 (m, 1H), 4.46 (m, 2H), 3.77 (m, 1H), 3.22 (m, 1H), 3.02 (m, 2H), 2.20 (m, 1H), 1.55 (m, 2H), 1.51 (s, 3H), 1.40 (m, 2H), 1.34 (s, 3H), 0.87 (m, 3H). ES-MS m/z 495 (MH$^+$).

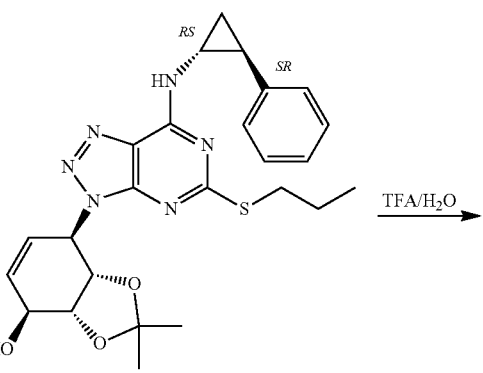

1h

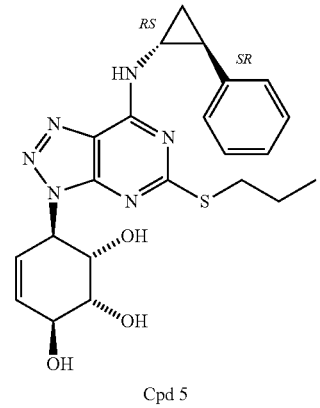

Cpd 5

Compound 1h (38 mg, 0.077 mmol) was treated with a solution of TFA/H$_2$O (4:1, 5 mL) and the mixture was stirred at rt overnight. The mixture was diluted with water and extracted with ethyl acetate. The organic layers were combined, dried (Na$_2$SO$_4$) and concentrated in vacuo. The residue was purified by flash chromatography (CH$_2$Cl$_2$/MeOH/ HOAc: 97:5:0.5) to give Compound 1 as a colorless solid (20 mg, 57%). $^1$H NMR (CD$_3$OD) δ 7.22 (m, 5H), 5.94 (m, 1H), 5.75 (m, 1H), 5.53 (m, 1H), 4.52 (m, 1H), 4.23 (m, 1H), 4.04 (m, 1H), 3.22 (m, 1H), 2.99 (m, 1H), 2.86 (m, 1H), 2.14 (m, 1H), 1.49 (m, 4H), 0.84 (t, J=7.2 Hz, 3H). ES-MS m/z 455 (MH$^+$).

Using the procedure of Example 1 or other conventional methods known to those skilled in the art, other compounds representative of the present invention were prepared (wherein MS represents ES-MS m/z (MH$^+$)):

| Cpd | Name | MS |
|---|---|---|
| 1 | (1S,2R,3S,6R)-6-(7-butylamino-5-propylsulfanyl-[1,2,3]triazolo[4,5-d]pyrimidin-3-yl)-cyclohex-4-ene-1,2,3-triol | 395 |
| 2 | (1S,2R,3S,6R)-6-(5-propylsulfanyl-7-{[(2R)-tetrahydro-furan-2-ylmethyl]-amino}-[1,2,3]triazolo[4,5-d]pyrimidin-3-yl)-cyclohex-4-ene-1,2,3-triol | 423 |
| 3 | (1S,2R,3S,6R)-6-(5-propylsulfanyl-7-{[(2S)-tetrahydro-furan-2-ylmethyl]-amino}-[1,2,3]triazolo[4,5-d]pyrimidin-3-yl)-cyclohex-4-ene-1,2,3-triol | 423 |
| 4 | (1S,2R,3S,4R)-6-{7-[(furan-2-ylmethyl)-amino]-5-propylsulfanyl-[1,2,3]triazolo[4,5-d]pyrimidin-3-yl}-cyclohex-4-ene-1,2,3-triol | 419 |
| 6 | (1S,2R,3S,4R)-6-{7-[(1-ethyl-pyrrolidin-2-ylmethyl)-amino]-5-propylsulfanyl-[1,2,3]triazolo[4,5-d]pyrimidin-3-yl}-cyclohex-4-ene-1,2,3-triol | 450 |

-continued

| Cpd | Name | MS |
|---|---|---|
| 7 | (1S,2R,3S,4R)-6-[5-propylsulfanyl-7-(2-thiophen-2-yl-ethylamino)-[1,2,3]triazolo[4,5-d]pyrimidin-3-yl]-cyclohex-4-ene-1,2,3-triol | 449 |
| 8 | (1S,2R,3S,6R)-6-{7-[(1-methyl-1H-pyrrol-2-ylmethyl)-amino]-5-propylsulfanyl-[1,2,3]triazolo[4,5-d]pyrimidin-3-yl}-cyclohex-4-ene-1,2,3-triol | 432 |
| 9 | (1R,2R,4S,5S)-6-{7-[(1RS,2SR)-phenyl-cyclopropylamino]-5-propylsulfanyl-[1,2,3]triazolo[4,5-d]pyrimidin-3-yl}-cyclohexane-1,2,3,4,5-pentaol | 489 |
| 10 | (3aR,4S,7R,7aS)-2,2-dimethyl-7-{7-[(1RS,2SR)-2-phenyl-cyclopropylamino]-5-propylsulfanyl-[1,2,3]triazolo[4,5-d]pyrimidin-3-yl}-3a,4,7,7a-tetrahydro-benzo[1,3]dioxol-4-ol | 495 |
| 11 | [(1S,4R,5S,6S)-5,6-dihydroxy-4-{7-[(1RS,2SR)-2-phenyl-cycopropylamino]-5-propylsulfanyl-[1,2,3]triazolo[4,5-d]pyrimidin-3-yl}-cyclohex-2-enyloxy]-acetic acid | 513 |
| 12 | (1R,2R,4S,5S)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2,4,5-tetraol | 533 |
| 13 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohex-4-ene-1,2-diol | 499 |
| 14 | (1S,2R,3S,4R)-4-{7-[(1RS,2SR)-2-phenyl-cyclopropylamino]-5-propylsulfanyl-[1,2,3]triazolo[4,5-d]pyrimidin-3-yl}-cyclohexane-1,2,3-triol | 457 |
| 15 | (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2-diol | 501 |
| 16 | (1S,2R,3S,4R)-4-(5-propylsulfanyl-7-{[(2S)-tetrahydro-furan-2-ylmethyl]-amino}-[1,2,3]triazolo[4,5-d]pyrimidin-3-yl)-cyclohexane-1,2,3-triol | 425 |
| 17 | (1S,2R,3S,4R)-4-(5-propylsulfanyl-7-{[(2R)-tetrahydro-furan-2-ylmethyl]-amino}-[1,2,3]triazolo[4,5-d]pyrimidin-3-yl)-cyclohexane-1,2,3-triol | 425 |
| 18 | (1S,2R,3S,4R)-4-{7-[(furan-2-ylmethyl)-amino]-5-propylsulfanyl-[1,2,3]triazolo[4,5-d]pyrimidin-3-yl}-cyclohexane-1,2,3-triol | 421 |
| 19 | (1S,2R,3S,4R)-4-(7-butylamino-5-propylsulfanyl-[1,2,3]triazolo[4,5-d]pyrimidin-3-yl)-cyclohexane-1,2,3-triol | 397 |
| 20 | (1S,2R,3S,4R)-4-[5-propylsulfanyl-7-(2-thiophen-2-yl-ethylamino)-[1,2,3]triazolo[4,5-d]pyrimidin-3-yl]-cyclohexane-1,2,3-triol | 451 |
| 21 | (1S,2R,3S,4R)-4-{7-[(1-ethyl-pyrrolidin-2-ylmethyl)-amino]-5-propylsulfanyl-[1,2,3]triazolo[4,5-d]pyrimidin-3-yl}-cyclohexane-1,2,3-triol | 452 |
| 22 | (1S,2R,3S,4R)-4-{7-[(3R)-1-benzyl-pyrrolidin-3-ylamino]-5-propylsulfanyl-[1,2,3]triazolo[4,5-d]pyrimidin-3-yl}-cyclohexane-1,2,3-triol | 500 |

Biological Examples

The ability of the compounds of the present invention to ameliorate, treat or prevent a thrombin mediated disease, disorder or condition was determined using the following procedures.

Example 1

High Throughput Screening Assay

A FLIPR Calcium Assay Transducing Gi-Coupled Signaling to the Gq Pathway

The ADP P2Y12 subtype is a Gi coupled GPCR, which mediates inhibition of adenylate cyclase leading to decreased cAMP while Gq proteins primarily activate phospholipase C, which stimulates inositol-1,4,5-triphosphate ($IP_3$) formation and a subsequent increase in intracellular $Ca^{2+}$ concentration, which can be easily measured by FLIPR. Prior to the development of a method to convert a Gi coupled GPCR signaling to a Gq coupled GPCR signaling, a significant barrier existed for the functional testing and screening of Gi coupled GPCRs. One popular method, GTPγS migration, is slow, produces a small signal and generates radioactive waste. The discovery that a small switch in the amino acid sequence in the Gi protein could convert it to a protein mediating a Gq coupled response has led to the development of robust, high throughput assays for this valuable receptor subtype.

The FLIPR-based HTS assay transducing the Gi signaling to the Gq pathway is described below.

pcDNA3hygroP2Y12 containing a hygromycin resistance gene and pLEC1-$G_{qi5}$-HA containing a neomycin resistance gene (licensed from Molecular Devices, Sunnyvale, Calif.) were co-transfected into Human embryonic kidney (HEK) 293 cells with SuperFect (Qiagen, Valencia, Calif.). Cell clones were selected in the presence of 600 µg/ml hygromycin B (Life Technologies, Carlsbad, Calif.) and 1 mg/ml of G418 (Mediatech, Herndon, Va.). Drug resistant colonies were picked and screened by FLIPR and the gene expression was further confirmed by RT-PCR. Positive clones were maintained in growth medium (DMEM supplemented with 10% FBS, 1xp/s) containing 400 µg/ml of G418 and 200 µg/ml of hygromycin.

The day before the assay, cells are seeded in clear, flat-bottom black-wall, tissue culture treated polystyrene 96- or 384-well plates and incubated at 37° C., 5% $CO_2$. 50 µl of complete dye loading solution (FLIPR Calcium Assay Kit, Molecular Devices) was added to each well containing 100 µl of culture media. The cells were incubated for at least 30 min at 37° C., in 5% $CO_2$ before initiating the assay on the FLIPR. The agonist effect of ADP was tested and $EC_{50}$ was determined prior to compound testing. The $EC_{60-70}$ dose was used.

The antagonist compounds were prepared at 4× and the agonists were diluted at 5× the concentration desired in the test wells, and then aliquoted into the sample plates. The sample plates and the cell plate were placed in the FLIPR assay chamber. A first addition (50 µl) was made at the start of reading and a second addition (50 µl) was made after 5 min of reading. Raw fluorescence data was exported for each well and tabulated versus time within an ASCII file. Data was then imported into Excel and the peak response over the basal level was determined. The percent inhibition for each compound was calculated by the change in fluorescent density as a % inhibition of the control ADP response to obtain an $IC_{50}$, as shown in Table 1 (wherein N/A means Not Applicable).

TABLE 1

Inhibition of Calcium Mobilization ($IC_{50}$ µM)

| Cpd | $IC_{50}$ | SEM |
|---|---|---|
| 1 | 2.117 | 0.045 |
| 2 | >30 | N/A |
| 3 | >30 | N/A |
| 4 | >30 | N/A |
| 5 | 0.745 | 0.086 |
| 6 | >30 | N/A |
| 7 | 14.720 | 0.576 |
| 8 | >30 | N/A |
| 9 | 2.959 | 0.757 |
| 10 | >30 | N/A |
| 11 | 2.198 | 0.093 |
| 12 | 6.900 | N/A |
| 13 | >30 | N/A |
| 14 | 0.456 | 0.164 |
| 15 | 2.634 | 0.429 |
| 16 | >30 | N/A |
| 17 | >30 | N/A |
| 18 | >30 | N/A |
| 19 | 2.935 | 0.773 |
| 20 | >30 | N/A |
| 21 | >30 | N/A |
| 22 | >30 | N/A |

Example 2

Receptor Binding Assay

A whole cell-binding assay for 2-MeS [$^3$H]-ADP (Custom synthesized by Amersham BioScience, Piscataway, N.J.) to the P2Y12 receptor was performed.

A P2Y12 cDNA containing hygromycin resistant gene was transfected in HEK 293 cells. A stable cell line was obtained by a cloning selection method. The cells were cultured in DMEM supplemented with 10% FBS and 1× of p/s.

On the day of the assay, the cells were harvested and resuspended in 0.25% BSA-DMEM and adjusted to a cell concentration of $1.6 \times 10^6$/ml. 15 µl of each compound was mixed with 120 µl of cell suspension in 96 well assay plates and incubated for 5 min prior to the addition of the radiolabeled ligand 2-MeS[$^3$H]-ADP (3 nM final in 0.25% BSA-DMEM) or unlabeled 2-MeS[$^3$H]-ADP (for non-specific binding). The reaction was then incubated for 30 min at 37° C. and stopped by adding cold DMEM. The labeled and unlabeled cells were separated by a filtration method using a Packard Filtermate 196 on to the unifilter-96 GF/B plate. The plates were dyed in a 37° C. oven for 1-2 hours and 50 µl of MicroScint-20 (PerkinElmer) was added to each well. The radioactivity was measured using a TOPCOUNT beta counter (Packard). The percent inhibition for each compound was calculated by the change in radioactivity as a % inhibition of the control to obtain an $IC_{50}$, as shown in Table 2.

TABLE 2

Inhibition of Receptor Binding ($IC_{50}$ µM)

| Cpd | $IC_{50}$ | SEM |
|---|---|---|
| 1 | 9.029 | 2.472 |
| 3 | 4.755 | 2.369 |
| 5 | 2.105 | 0.589 |
| 7 | 2.270 | 0.403 |
| 9 | 5.040 | 2.066 |
| 11 | 1.490 | 0.633 |
| 12 | 2.200 | 0.776 |
| 13 | 8.564 | 2.956 |
| 14 | 1.349 | 0.441 |
| 15 | 6.598 | 2.719 |

Example 3

In Vitro Platelet Aggregation

Platelet aggregation studies were performed according to a published method (Bednar, B., Condra, C., Gould, R. J., and Connolly, T. M., Throm. Res., 77:453-463 (1995). Platelet-rich plasma (PRP) concentrates prepared from healthy volunteers who were aspirin free for at least 7 days by venipuncture using ACD-A as anticoagulant was purchased from Biological Specialties, Inc. (Colmar, Pa.). PRP was centrifuged at 730 g for 15 min. The platelet pellet was washed twice in CGS buffer (13 mM sodium citrate, 30 mM glucose, 120 mM NaCl, pH 6.5) containing 1 µ/ml apyrase (grade V, Sigma-Aldrich, St. Louis, Mo.), 1 mM EGTA, and resuspended in Tyrode's buffer (140 mM NaCl, 2.7 mM KCl, 12 mM $NaHCO_3$, 0.76 mM $Na_2HPO_4$, 5.5 mM dextrose, 5.0 mM Hepes, 0.2% BSA, pH 7.4). The platelets were diluted to $3 \times 10^8$ platelets/ml and kept >45 min at 37° C. before use. 105 µl of washed platelets, 2 mM $CaCl_2$ and 2.5 mM of fibrinogen were added to a 96-well microliter plate.

Platelet aggregation was initiated by the addition of serial concentrations of ADP (BioData Corp. Horsham, Pa.). Buffer was added to one set of control wells. The assay plate was stirred constantly and intermittently placed in a microplate reader (Softmax, Molecular Devices, Menlo Park, Calif.) to read optical density (650 nm) at 0 and 5 minutes after the addition of the compound solutions. Aggregation was calculated as the decrease in optical density between the time 0- and 5-min measurements and expressed as % of aggregation. For the inhibition assay, platelet aggregation was conducted as described above except for compound additions. Test compounds were prepared in 100% DMSO and stored.

On the day of the assay, test compounds were diluted in the buffer containing 3% of DMSO as a 10× working solution. 15 µl of compound solutions were added to 105 µl of platelets 5 min prior to the addition of $CaCl_2$ and fibrinogen. Platelet aggregation was initiated by the addition of an agonist which had been shown to achieve 60-70% aggregation. Antagonist potency was estimated as a % inhibition of the control ADP response to obtain an $IC_{50}$, as shown in Table 3.

TABLE 3

Inhibition of Platelet Aggregation ($IC_{50}$ µM)

| Cpd | $IC_{50}$ | SEM |
|---|---|---|
| 1 | 15.180 | 1.988 |
| 5 | 5.050 | 1.374 |
| 9 | 15.023 | 3.743 |
| 11 | 2.913 | 0.230 |
| 14 | 3.103 | 0.341 |
| 17 | >30 | N/A |
| 21 | >30 | N/A |

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. The disclosure of these publications is hereby incorporated by reference into this application to describe more fully the state of the art to which this invention pertains.

What is claimed is:

1. A compound of Formula (I):

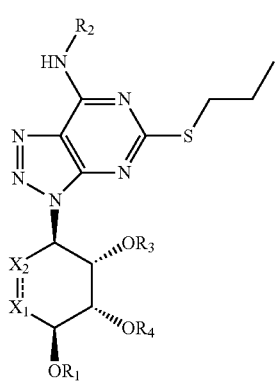

wherein:
R₁ is selected from hydrogen, hydroxy-C$_{1-8}$alkyl, C$_{1-8}$alkoxy-C$_{1-8}$alkyl or carboxy-C$_{1-8}$alkyl;
R₂ is selected from C$_{1-8}$alkyl, C$_{1-8}$alkoxy-C$_{1-8}$alkyl, C$_{1-8}$alkyl-thio-C$_{1-8}$alkyl, C$_{3-8}$cycloalkyl, C$_{3-8}$cycloalkyl-C$_{1-8}$alkyl, phenyl-C$_{1-8}$alkyl, heterocyclyl, heterocyclyl-C$_{1-8}$alkyl, heteroaryl-C$_{1-8}$alkyl or halo-C$_{1-8}$alkyl,
wherein each instance of C$_{3-8}$cycloalkyl, heterocyclyl and heteroaryl is optionally substituted with C$_{1-8}$alkyl, phenyl or benzyl, wherein phenyl is optionally substituted with C$_{1-4}$alkyl, C$_{1-4}$alkoxy, amino, C$_{1-4}$alkyl-amino, hydroxy, cyano, halo-C$_{1-4}$alkyl or halogen;
R₃ and R₄ are each selected from hydrogen or are optionally taken together with the carbon atoms of attachment to form a heterocyclyl ring having 5 or 6 ring members, wherein said heterocyclyl ring is optionally substituted with one or two C$_{1-8}$alkyl substituents; and,
X₁ and X₂ are each selected from CH, CH₂ or CH(OH), wherein when either X₁ or X₂ is CH, then X₁ and X₂ must both be CH and the dashed line represents a double bond,
and enantiomers, stereoisomers, and pharmaceutically acceptable salts thereof.

2. The compound of claim 1, wherein R₁ is selected from hydrogen, hydroxy-C$_{1-8}$alkyl or carboxy-C$_{1-8}$alkyl.

3. The compound of claim 1, wherein
R₂ is selected from C$_{1-4}$alkyl, cyclopropyl, heterocyclyl, pyrrolidinyl-C$_{1-4}$alkyl, tetrahydrofuranyl-C$_{1-4}$alkyl, furanyl-C$_{1-4}$alkyl, thienyl-C$_{1-4}$alkyl or pyrrolyl-C$_{1-4}$alkyl,
wherein cyclopropyl is optionally substituted with phenyl, wherein phenyl is optionally substituted with halogen, and
wherein pyrrolyl and pyrrolidinyl are each optionally substituted with C$_{1-4}$alkyl or benzyl.

4. The compound of claim 1, wherein R₃ and R₄ are each selected from hydrogen or are optionally taken together with the carbon atoms of attachment to form a [1,3]dioxolanyl ring, wherein said ring is optionally substituted with one or two C$_{1-8}$alkyl substituents.

5. The compound of claim 1, wherein X₁ and X₂ are each selected from CH₂ or CH(OH).

6. The compound of claim 1, wherein X₁ and X₂ are each CH and the dashed line represents a double bond.

7. The compound of claim 1, wherein
R₁ is selected from hydrogen, hydroxy-C$_{1-4}$alkyl or carboxy-C$_{1-4}$alkyl;
R₂ is selected from C$_{1-4}$alkyl, cyclopropyl, heterocyclyl, pyrrolidinyl-C$_{1-4}$alkyl, tetrahydrofuranyl-C$_{1-4}$alkyl, furanyl-C$_{1-4}$alkyl, thienyl-C$_{1-4}$alkyl or pyrrolyl-C$_{1-4}$alkyl,
wherein cyclopropyl is optionally substituted with phenyl, wherein phenyl is optionally substituted with halogen, and
wherein pyrrolyl and pyrrolidinyl are each optionally substituted with C$_{1-4}$alkyl or benzyl;
R₃ and R₄ are each hydrogen; and
X₁ and X₂ are each selected from CH, CH₂ or CH(OH), wherein when either X₁ or X₂ is CH, then X₁ and X₂ must both be CH and the dashed line represents a double bond.

8. A compound of claim 1 selected from the group consisting of:
(1S,2R,3S,6R)-6-(7-butylamino-5-propylsulfanyl-[1,2,3]triazolo[4,5-d]pyrimidin-3-yl)-cyclohex-4-ene-1,2,3-triol,
(1S,2R,3S,6R)-6-(5-propylsulfanyl-7-{[(2R)-tetrahydrofuran-2-ylmethyl]-amino}-[1,2,3]triazolo[4,5-d]pyrimidin-3-yl)-cyclohex-4-ene-1,2,3-triol,
(1S,2R,3S,6R)-6-(5-propylsulfanyl-7-{[(2S)-tetrahydrofuran-2-ylmethyl]-amino}-[1,2,3]triazolo[4,5-d]pyrimidin-3-yl)-cyclohex-4-ene-1,2,3-triol,
(1S,2R,3S,4R)-6-{7-[(furan-2-ylmethyl)-amino]-5-propylsulfanyl-[1,2,3]triazolo[4,5-d]pyrimidin-3-yl}-cyclohex-4-ene-1,2,3-triol,
(1S,2R,3S,6R)-6-{7-[(1RS,2SR)-2-phenyl-cyclopropylamino]-5-propylsulfanyl-[1,2,3]triazolo[4,5-d]pyrimidin-3-yl}-cyclohex-4-ene-1,2,3-triol,
(1S,2R,3S,4R)-6-{7-[(1-ethyl-pyrrolidin-2-ylmethyl)-amino]-5-propylsulfanyl-[1,2,3]triazolo[4,5-d]pyrimidin-3-yl}-cyclohex-4-ene-1,2,3-triol,
(1S,2R,3S,4R)-6-[5-propylsulfanyl-7-(2-thiophen-2-yl-ethylamino)-[1,2,3]triazolo[4,5-d]pyrimidin-3-yl]-cyclohex-4-ene-1,2,3-triol,
(1S,2R,3S,6R)-6-{7-[(1-methyl-1H-pyrrol-2-ylmethyl)-amino]-5-propylsulfanyl-[1,2,3]triazolo[4,5-d]pyrimidin-3-yl}-cyclohex-4-ene-1,2,3-triol,
(1R,2R,4S,5S)-6-{7-[(1RS,2SR)-phenyl-cyclopropylamino]-5-propylsulfanyl-[1,2,3]triazolo[4,5-d]pyrimidin-3-yl}-cyclohexane-1,2,3,4,5-pentaol,
(3aR,4S,7R,7aS)-2,2-dimethyl-7-{7-[(1RS,2SR)-2-phenyl-cyclopropylamino]-5-propylsulfanyl-[1,2,3]triazolo[4,5-d]pyrimidin-3-yl}-3 a,4,7,7a-tetrahydrobenzo[1,3]dioxol-4-ol,
[(1S,4R,5S,6S)-5,6-dihydroxy-4-{7-[(1RS,2SR)-2-phenyl-cyclopropylamino]-5-propylsulfanyl-[1,2,3]triazolo[4,5-d]pyrimidin-3-yl}-cyclohex-2-enyloxy]-acetic acid,
(1R,2R,4S,5S)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2,4,5-tetraol,
(1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohex-4-ene-1,2-diol,
(1S,2R,3S,4R)-4-{7-[(1RS,2SR)-2-phenyl-cyclopropylamino]-5-propylsulfanyl-[1,2,3]triazolo[4,5-d]pyrimidin-3-yl}-cyclohexane-1,2,3-triol,
(1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2-diol,
(1S,2R,3S,4R)-4-(5-propylsulfanyl-7-{[(2R)-tetrahydrofuran-2-ylmethyl]-amino}-[1,2,3]triazolo[4,5-d]pyrimidin-3-yl)-cyclohexane-1,2,3-triol,
(1S,2R,3S,4R)-4-(5-propylsulfanyl-7-{[(2R)-tetrahydrofuran-2-ylmethyl]-amino}-[1,2,3]triazolo[4,5-d]pyrimidin-3-yl)-cyclohexane-1,2,3-triol,
(1S,2R,3S,4R)-4-{7-[(furan-2-ylmethyl)-amino]-5-propylsulfanyl-[1,2,3]triazolo[4,5-d]pyrimidin-3-yl}-cyclohexane-1,2,3-triol,
(1S,2R,3S,4R)-4-(7-butylamino-5-propylsulfanyl-[1,2,3]triazolo[4,5-d]pyrimidin-3-yl)-cyclohexane-1,2,3-triol,
(1S,2R,3S,4R)-4-[5-propylsulfanyl-7-(2-thiophen-2-yl-ethylamino)-[1,2,3]triazolo[4,5-d]pyrimidin-3-yl]-cyclohexane-1,2,3-triol,
(1S,2R,3S,4R)-4-{7-[(1-ethyl-pyrrolidin-2-ylmethyl)-amino]-5-propylsulfanyl-[1,2,3]triazolo[4,5-d]pyrimidin-3-yl}-cyclohexane-1,2,3-triol, and
(1S,2R,3S,4R)-4-{7-[(3R)-1-benzyl-pyrrolidin-3-ylamino]-5-propylsulfanyl-[1,2,3]triazolo[4,5-d]pyrimidin-3-yl}-cyclohexane-1,2,3-triol.

9. The compound of claim 8, wherein the compound is selected from the group consisting of:

(1S,2R,3S,6R)-6-(7-butylamino-5-propylsulfanyl-[1,2,3]triazolo[4,5-d]pyrimidin-3-yl)-cyclohex-4-ene-1,2,3-triol, (1S,2R,3S,6R)-6-(5-propylsulfanyl-7-{[(2S)-tetrahydrofuran-2-ylmethyl]-amino}-[1,2,3]triazolo[4,5-d]pyrimidin-3-yl)-cyclohex-4-ene-1,2,3-triol, (1S,2R,3S,6R)-6-{7-[(1RS,2SR)-2-phenyl-cyclopropylamino]-5-propylsulfanyl-[1,2,3]triazolo[4,5-d]pyrimidin-3-yl}-cyclohex-4-ene-1,2,3-triol, (1S,2R,3S,4R)-6-[5-propylsulfanyl-7-(2-thiophen-2-ylethylamino)-[1,2,3]triazolo[4,5-d]pyrimidin-3-yl]-cyclohex-4-ene-1,2,3-triol, (1R,2R,4S,5S)-6-{7-[(1RS,2SR)-phenyl-cyclopropylamino]-5-propylsulfanyl-[1,2,3]triazolo[4,5-d]pyrimidin-3-yl}-cyclohexane-1,2,3,4,5-pentaol,

[(1S,4R,5S,6S)-5,6-dihydroxy-4-{7-[(1RS,2SR)-2-phenyl-cyclopropylamino]-5-propylsulfanyl-[1,2,3]triazolo[4,5-d]pyrimidin-3-yl}-cyclohex-2-enyloxy]-acetic acid, (1R,2R,4S,5S)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2,4,5-tetraol, (1S,2R,3S,4R)-4-{7-[(1RS,2SR)-2-phenyl-cyclopropylamino]-5-propylsulfanyl-[1,2,3]triazolo[4,5-d]pyrimidin-3-yl}-cyclohexane-1,2,3-triol, (1S,2S,3S,6R)-3-(2-hydroxy-ethoxy)-6-{7-[(1RS,2SR)-2-phenyl-cyclopropylamino]-5-propylsulfanyl-[1,2,3]triazolo[4,5-d]pyrimidin-3-yl}-cyclohexane-1,2-diol, and (1S,2R,3S,4R)-4-(7-butylamino-5-propylsulfanyl-[1,2,3]triazolo[4,5-d]pyrimidin-3-yl)-cyclohexane-1,2,3-triol.

10. A method for ameliorating, treating or preventing a platelet-mediated thrombotic disease, disorder or condition in a subject in need thereof comprising administering to the subject an effective amount of one or more compounds of claim 1 for inhibiting platelet activation, aggregation and degranulation or for promoting platelet disaggregation, or as anti-thrombotic agents.

11. The method of claim 10, wherein the effective amount of the compound is from about 0.001 mg/kg/day to about 300 mg/kg/day.

* * * * *